(12) United States Patent
Lu et al.

(10) Patent No.: US 6,667,825 B2
(45) Date of Patent: Dec. 23, 2003

(54) STABLE CONJUGATED POLYMER ELECTROCHROMIC DEVICES INCORPORATING IONIC LIQUIDS

(75) Inventors: Wen Lu, Santa Fe, NM (US); Benjamin R. Mattes, Santa Fe, NM (US); Andrei G. Fadeev, Santa Fe, NM (US); Baohua Qi, Albuquerque, NM (US)

(73) Assignee: Santa Fe Science and Technology, Inc., Santa Fe, NM (US)

( * ) Notice: Subject to any disclaimer, the term of this patent is extended or adjusted under 35 U.S.C. 154(b) by 0 days.

(21) Appl. No.: 10/037,483

(22) Filed: Jan. 3, 2002

(65) Prior Publication Data

US 2002/0191270 A1 Dec. 19, 2002

Related U.S. Application Data

(60) Provisional application No. 60/259,783, filed on Jan. 3, 2001.

(51) Int. Cl.[7] ............................................. G02F 1/15
(52) U.S. Cl. ........................................ 359/265; 359/271
(58) Field of Search ................................ 359/265–275

(56) References Cited

U.S. PATENT DOCUMENTS

| | | | | |
|---|---|---|---|---|
| 4,598,979 A | * | 7/1986 | Sugiuchi et al. | 359/273 |
| 5,637,421 A | * | 6/1997 | Poehler et al. | 429/303 |
| 6,245,847 B1 | * | 6/2001 | Green et al. | 524/418 |
| 6,498,358 B1 | * | 12/2002 | Lach et al. | 257/183 |

* cited by examiner

Primary Examiner—Jordan M. Schwartz
Assistant Examiner—Jessica Stultz
(74) Attorney, Agent, or Firm—The Law Offices of William W. Cochran, LLC; Samuel M. Freund

(57) ABSTRACT

Electrochemical synthesis of conjugated polymers in ionic liquids, achievement of electroactivity and electrochroism of conjugated polymers in ionic liquids, and the use of the resulting conjugated polymers for the fabrication of electrochromic devices incorporating ionic liquids as electrolytes are described.

20 Claims, 22 Drawing Sheets

Polyphenylene

Polyphenylenevinylene

Polyphenylenesulfide

Polyacetylene

Poly(p-pyridine)

Poly(p-pyridalvinylene)

Polypyrrole

Polyaniline

Polythiophene

Polythiophenevinylene

Polyfuran

Polyquinone

Pyridinium

Pyridazinium

Pyrimidinium

Pyrazinium

Imidazolium

Pyrazolium

Thriazolium

Oxazolium

Triazolium

Ammonium

Pyrrolidinium

Pyrrolinium

Pyrrolium

Piperidinium

STABLE CONJUGATED POLYMER ELECTROCHROMIC DEVICES INCORPORATING IONIC LIQUIDS

RELATED CASES

This patent application claims the benefit of Provisional Application No. 60/259,783 for "Stable Conjugated Polymer Electrochromic Devices Incorporating Ionic Liquids" which was filed on Jan. 3, 2001.

STATEMENT REGARDING FEDERAL RIGHTS

This invention was made with government support under Contract No. MDA972-99-C-0004 awarded by the U.S. Defense Advance Research Projects Agency to Santa Fe Science and Technology, Inc., Santa Fe, N. Mex. 87505. The government has certain rights in the invention.

FIELD OF THE INVENTION

The present invention relates generally to the fabrication of stable conjugated polymer electrochemical devices and, more particularly, to the development of stable conjugated polymer electrochromic devices incorporating ionic liquids. Conjugated polymers having electroactivity and electrochroism have also been electrochemically synthesized using ionic liquids as electrolytes as well as by chemical methods, and electrochromic devices fabricated therefrom.

BACKGROUND OF THE INVENTION

Electrochromic devices, such as displays and smart windows, are fabricated from electrochromic materials that change color in a persistent but reversible manner as the result of an electrochemical reaction. These devices find applications in a wide range of areas; as examples: in the optical and communication industry, as optical information displays and storage media; in the building industry, as architectural glazed windows for energy control and glare-reduction system for offices; in the automobile industry, as anti-glare rear-view mirrors and sun roofs for cars; in the armed services, as protective eyewear for soldiers and controllable canopies for aircrafts; and in daily life, as consumer sunglasses. Electrochromic rear-view mirrors for automobiles have already achieved considerable commercial success. Advantages of electrochromic devices (ED) over liquid crystalline displays (LCD) include transparency and flexibility. In contrast to LCDs, EDs do not polarize light; thus, ED images can be observed for over a large angular distribution.

The most successful and frequently used electrochromic materials to date are inorganic compounds such as $WO_3$, $MoO_3$ and $V_2O_5$. These materials are expensive to process which inevitably limits their commercial and industrial applications. Therefore, the use of conjugated polymers as electrochromic materials has become an important research area. In addition to low-cost, conjugated polymers have other advantages over inorganic compounds, such as good processibility for large-area applications, and color selectivity for varying the coloration of chosen regions.

To fabricate electrochromic devices, conjugated polymers are coated on conductive, transparent-glass electrodes such as indium tin oxide. The two principal methods for polymer coating are chemical and electrochemical. Electrochemical processes possess the following advantages when compared to chemical methods: (a) polymerization, doping and processing take place simultaneously when electrochemical methods are employed, while for chemical processing, the initial polymer synthesis must be followed by doping and subsequent processing; (b) polymer thickness is more readily controlled by monitoring the charge consumed; (c) polymer films produced using electrochemical processes often exhibit higher conductivity; and (d) polymer properties are more readily varied by changing dopants.

Generally, the exclusion of moisture/water is of critical importance during the fabrication of solid-state electrochemical devices to ensure the high performance and long-term operation of the devices. Moisture/water may be introduced at any time during the fabrication process of electrochemical devices, including the preparation of polymer electrodes, the preparation of electrolytes and the assembly of the devices. Electrochemical synthesis and deposition of conjugated polymers can be carried out either in aqueous or non-aqueous electrolytes. If aqueous electrolytes are employed, the resulting polymers must be subjected to drying processes, preferably under vacuum, prior to use. For the frequently studied electrochromic material polyaniline, other problems have been identified relating to the electrochemical synthesis of polyaniline in aqueous electrolyte systems; for example, degradation of polyaniline during polarization (See, e.g., T. Kobayashi et al., *J. Electroanal Chem.* 177, 273 (1984)); and decrease in electrochemical activity due to nucleophilic attack on the polymer by $OH^-$ (See, e.g., T. Osaka et al., *J. Electrochem. Soc.* 136, 306 (1989)).

As a result, synthesis of conjugated polymers in non-aqueous electrolytes has generated extensive attention (See, e.g., T. Osaka, et al., *J. Electrochem. Soc.*, 1991, 138 (10), 2853. and K. Yamada et al., *J. Electroanal. Chem.*, 1995, 394, 71.). Evaporation of the organic solvents employed in the synthesis and the absorption of moisture to varying degrees by these solvents affects the long-term operation of the subsequently fabricated devices and makes it desirable to prepare these conjugated polymers in a dry glove box.

Additionally, moisture may be introduced during the preparation of the electrolytes used for device fabrication and the final assembly of the devices in air. The operating voltage and lifetime of the resulting devices are affected by the water content of the electrolytes resulting from the miscibility with water of the organic solvents employed. The evaporation of the organic solvents also limits the long-term operation of the devices. Thus, lack of volatility and lack of miscibility with water are important properties of electrolytes for the fabrication of durable and stable electrochemical devices.

Ionic liquids have received considerable attention as electrolytes in various electrochemical devices (See, e.g., A. B. McEwen et al., *Electrochemical Capacitors II*, F. M. Delnick et al., Editors, PV 96–25, p.313; V. R. Koch et al., *J. Electrochem. Soc.* 142, L116 (1995); V. R. Koch et al., *J. Electrochem. Soc.* 143, 788 (1996); J. S. Wilkes, and M. J. Zaworotko, *J. Chem. Soc. Commun.* p.965 (1992); R. T. Carlin et al., *J. Electrochem. Soc.* 141, L73 (1994); P. Bonhôte et al., *Inorg. Chem.* 35, 1168 (1996); and N. Papageorgiou et al., *J. Electrochem. Soc.* 143, 3099 (1996)). However, the use of ionic liquids as electrolytes for the fabrication and development of conjugated polymer electrochemical devices has not been previously addressed, and the study of ionic liquids as electrolytes in conjugated polymer electrochemistry is limited. Several electroactive polymers (polypyrrole, polythiophene and polyaniline) have been prepared in ionic liquids and the resulting polymer films have exhibited electroactivity in these ionic liquids (See, e.g., P. G. Pickup and R. A. Osteryoung, *J. Am. Chem. Soc.*, 106, 2294 (1984); P. G. Pickup and R. A. Osteryoung, *J.*

*Electroanal Soc.* 195, 271 (1985); L. Janiszewska and R. A. Osteryoung, *J. Electrochem. Soc.* 134, 2787 (1987); L. Janiszewska and R. A. Osteryoung, *J. Electrochem. Soc.* 135, 116 (1988); J. Tang and R. A. Osteryoung, *Synth. Met* 45, 1 (1991); J. Tang and R. A. Osteryoung, *Synth. Met.* 44, 307 (1991); and J. Tang et al., *J. Phys. Chem.* 96, 3531 (1992)). The research described in these papers was performed using aluminum chloride-1-ethyl-3-methylimidazolium chloride ($AlCl_3$-IMCl) as an electrolyte. U.S. Pat. No. 5,827,602 which issued to V. R. Koch et al. asserts that a disadvantage of these ionic liquids and a problem with any ionic liquid containing a strong Lewis acid such as $AlCl_3$, is the liberation of toxic gases when the ionic liquid is exposed to moisture. Additionally, the high reactivity of the Lewis acids used as a component of the ionic liquids limits the types of organic and inorganic compounds which are stable in these media. Typically, room-temperature ionic liquids containing Lewis acids decompose below 150° C.

Accordingly, it is an object of the present invention to provide a method for producing durable and stable conjugated polymer electrochromic devices using ionic liquids as electrolytes.

Another object of the present invention is to provide an electrochemical synthesis of conjugated polymers in ionic liquids.

Yet another object of the invention is to achieve electroactivity and electrochroism in conjugated polymers in contact with ionic liquids.

Additional objects, advantages and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

SUMMARY OF THE INVENTION

To achieve the foregoing and other objects, and in accordance with the purposes of the present invention as embodied and broadly described herein, the method for preparing an electroactive conjugated polymer includes the steps of: immersing a pair of electrodes in an ionic liquid solution containing the monomeric form of the conjugated polymer; and applying a voltage between the electrodes in the pair of electrodes until a desired quantity of conjugated polymer which is stable in the presence of the ionic liquid is deposited on one of the electrodes in the pair of electrodes.

Preferably, the voltage applied between the electrodes in the pair of electrodes can be a constant voltage, a voltage which establishes a constant current between the electrodes or a voltage cycled at a chosen scan rate.

It is preferred that the ionic liquid is stable in the presence of water.

In another aspect of the present invention in accordance with its objects and purposes, the electrochromic device hereof includes: a first electrically conducting substrate; a second electrically conducting substrate spaced apart from the first substrate; a first conjugated polymer deposited onto the surface of the first substrate facing the second substrate; a second conjugated polymer deposited onto the surface of the second substrate facing said first substrate; an ionic liquid electrolyte disposed between and in electrical contact with the first conjugated polymer and the said second conjugated polymer; and an electrical power supply for applying a voltage between the first substrate and the second substrate.

Preferably, the first conjugated polymer includes an anodically coloring conjugated polymer and the second conjugated polymer includes a cathodically coloring conjugated polymer.

It is preferred that the first substrate and the second substrate include conductive and optically transparent substrates.

It is also preferred that the deposited conjugate polymer is stable in the presence of the ionic liquid.

Preferably also, the ionic liquid is stable in the presence of water.

Benefits and advantages of the present invention include the preparation of conjugated polymers in ionic liquids in the absence of moisture and oxygen so that no drying is required before the polymers are incorporated into electrochromic devices. Moreover, there is less degradation over time of the resulting polymers which results in longer lifetimes therefor. Use of ionic liquids permits high-performance electrochromic devices having lower operating voltages and increased speed for coloration changes to be fabricated.

BRIEF DESCRIPTION OF THE DRAWINGS

The accompanying drawings, which are incorporated in and form a part of the specification, illustrate several embodiments of the present invention and, together with the description, serve to explain the principles of the invention. In the drawings:

FIGS. 1a–1c show examples of conjugated polymers suitable for use in the electrochromic devices of the present invention, while

DETAILED DESCRIPTION

Briefly, the present invention includes methods for electrochemically synthesizing conjugated polymers in ionic liquids, achieving electroactivity and electrochroism for conjugated polymers in ionic liquids, and fabricating conjugated polymer electrochromic devices including direct addressing displays, multiplex addressing displays, and large area windows with ionic liquids as electrolytes. As used herein, the term ionic liquid solution includes mixtures of ionic liquids and solutions of ionic solids dissolved in an ionic liquid. An example of the latter solution is LiClO$_4$ dissolved in [BMIM][BF$_4$].

Reference will now be made in detail to the present preferred embodiments of the invention, examples of which are illustrated in the accompanying drawings. Similar or identical structure is identified by identical callouts.

Figure 1A:
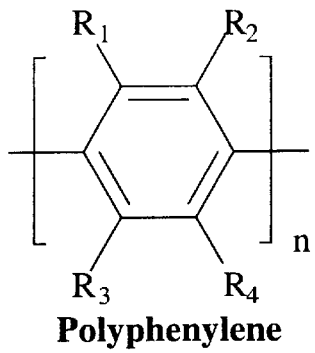
Figure 1A:
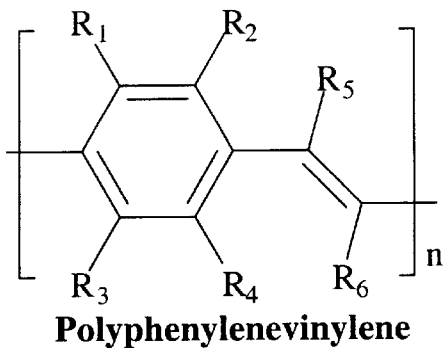
Figure 1A:
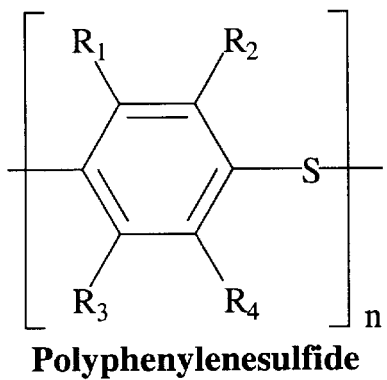
Figure 1A:
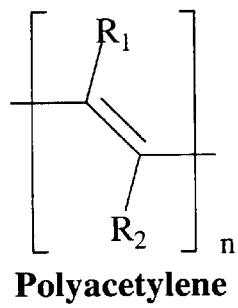
Figure 1A:
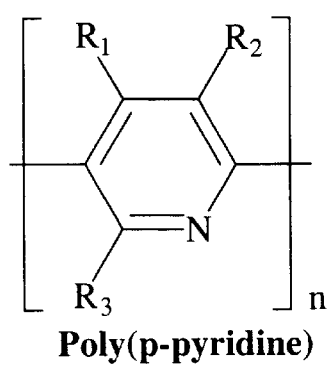
Figure 1A:
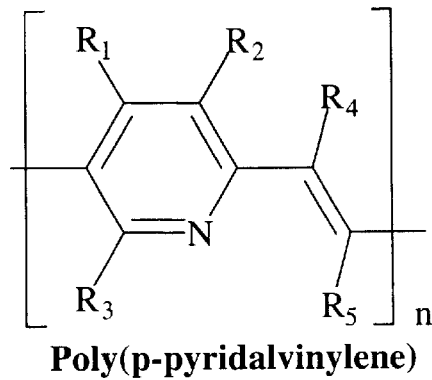
Figure 1B:
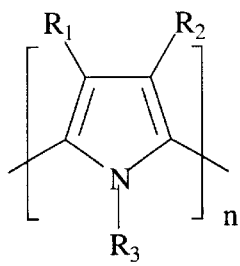
Figure 1B:
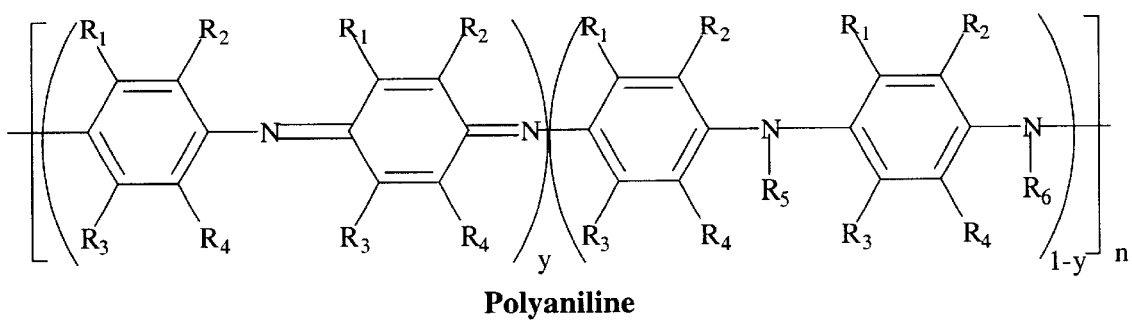
Figure 1B:
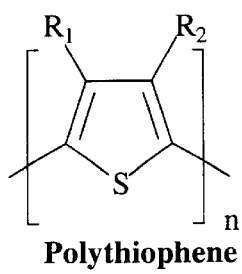
Figure 1B:
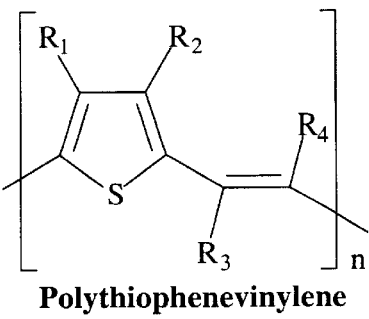
Figure 1B:
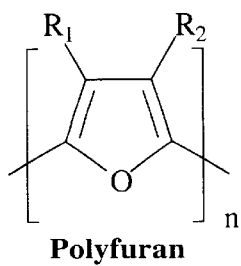
Figure 1B:
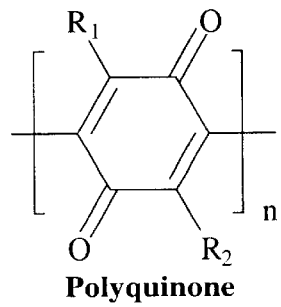
Figure 1C:
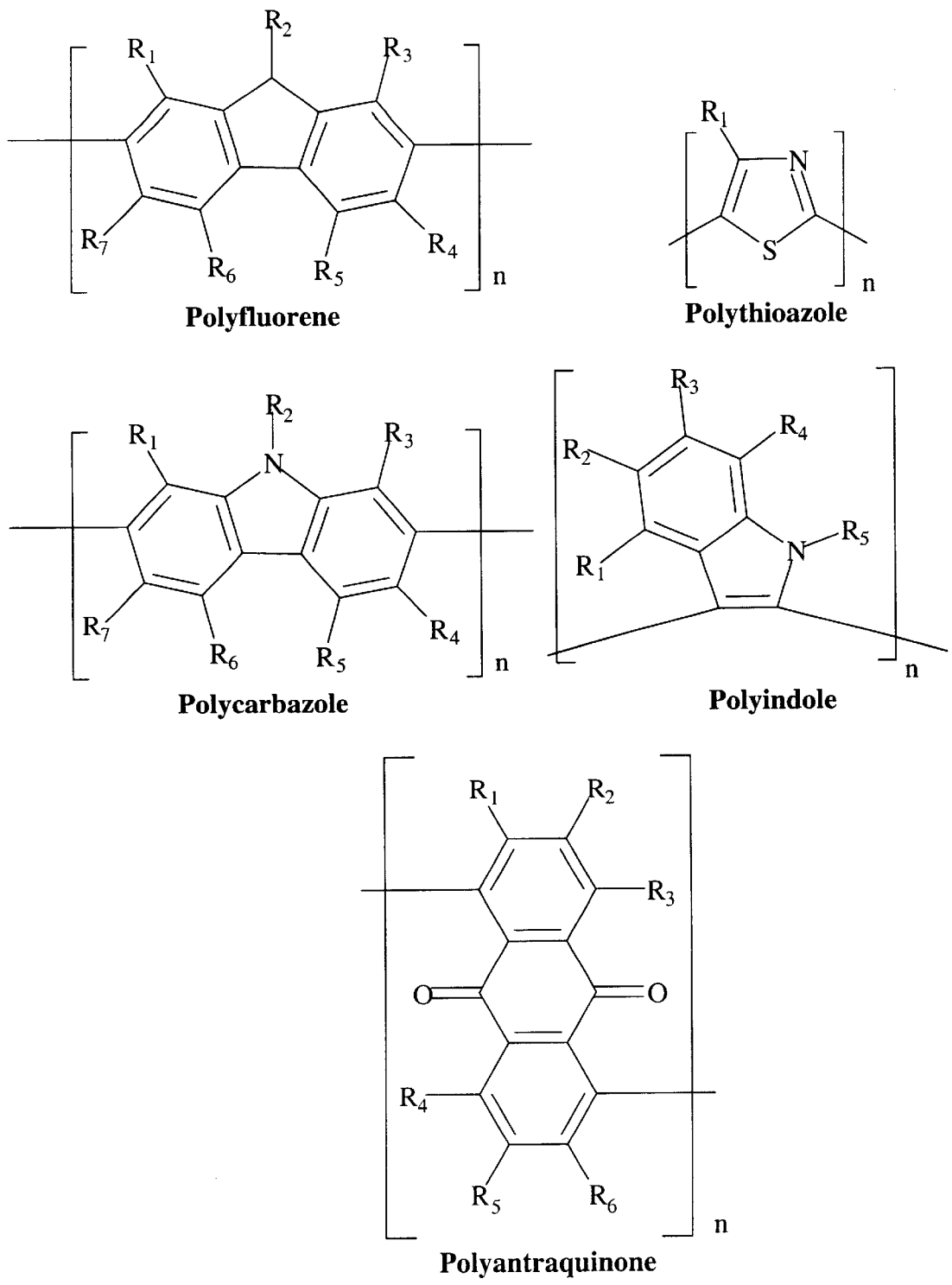
Figure 1D:
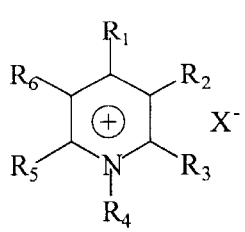
FIG. 1d shows examples of ionic liquids based on various monocations.
Figure 1D:
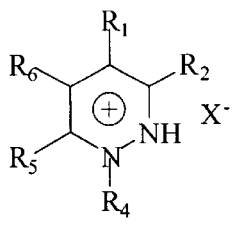
Figure 1D:
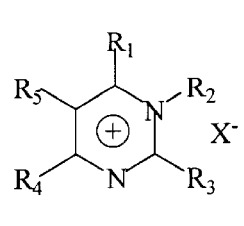
Figure 1D:
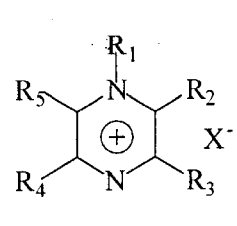
Figure 1D:
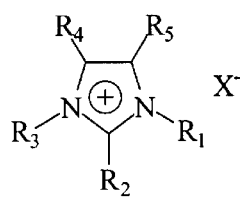
Figure 1D:
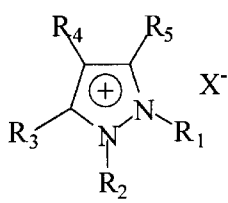
Figure 1D:
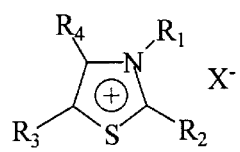
Figure 1D:
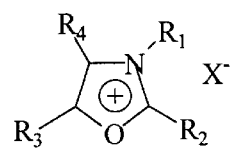
Figure 1D:
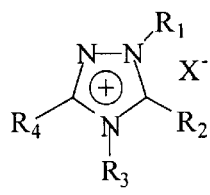
Figure 1D:
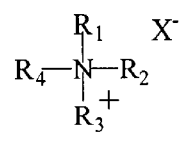
Figure 1D:
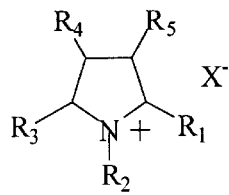
Figure 1D:
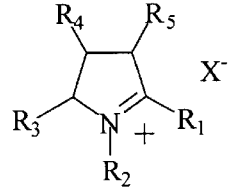
Figure 1D:
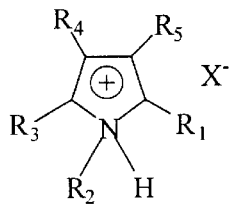
Figure 1D:
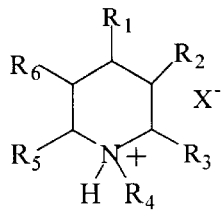
Figure 1E:
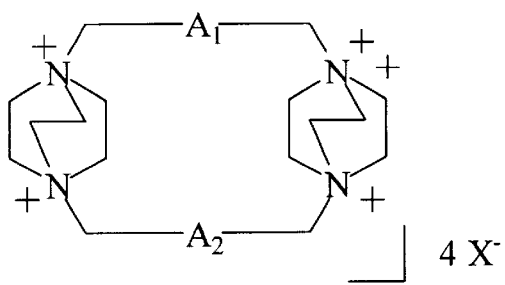
FIG. 1e shows examples of ionic liquids based on various polycations.
Figure 1E:
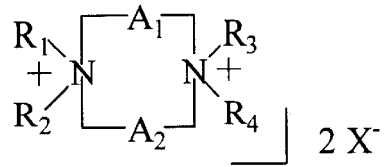
Figure 1E:
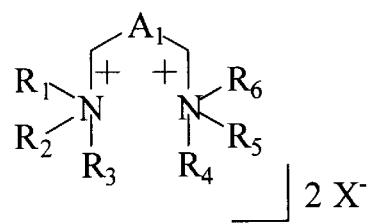
Figure 1E:
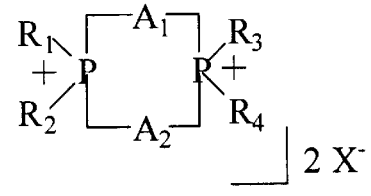

FIGS. 1a–1c show examples of conjugated polymers suitable for use in the electrochromic devices of the present invention, including the polymers: polyphenylene, polyphenylenevinylene, polyphenylenesulfide, polyfluorene, polypyridine, polypyridalvinylene, polypyrrole, polyaniline, polythiophene, polythiophenevinylene, polyfuran, polyacetylene, polyquinone, polyantraquinone, polycarbazole, polyindole, pollythioazole and derivatives thereof, while FIG. 1d shows examples of ionic liquids based on various monocations, and FIG. 1e shows examples of ionic liquids based on various polycations.

For polyphenylene, polyphenylenevinylene, and polyphenylenesulfide and for the monomers and oligomers of the monomers of these polymers, derivatives are defined where R$_1$, R$_2$, R$_3$ and R$_4$ are independently selected from the group consisting of a hydrogen atom or a nonconjugated substituent, such as, for example, hydrocarbyls, substituted hydrocarbyls, hydrocarbyloxys and poly(oxyalkylene)s. They may be straight chain but more typically are branched. The term "hydrocarbyl" refers to an organic radical primarily composed of carbon and hydrogen which may be aliphatic, alicyclic, aromatic or combinations thereof. It includes, without limitation "alkyls", "alkenyls", and "aryls" and "cycloalkyls". The term "substituted hydrocarbyl" refers to a hydrocarbyl group having from 1 to 3 substituents selected from the group consisting of hydroxy, acyl, acylamino, acyloxy, alkoxy, alkenyl, alkynyl, amino, aminoacyl, aryl, aryloxy, carboxy, carboxyalkyl, cyano, cycloalkyl, guanidino, halo, heteroaryl, heterocyclic, nitro, thiol, thioaryloxy, thioheteroaryloxy, and the like. Preferred substituents include hydroxy and cyano. The term "hydrocarbyloxy" refers to an organic radical primarily composed of carbon, oxygen and hydrogen which may be aliphatic, alicyclic, aromatic or combinations thereof. It includes, without limitation "alkoxys", "alkoxyalkyls" and "aryloxys".

The term "poly(oxyalkylene)" refers to a polyether having on average from about 2 to about 100 oxyalkylene units where the alkylene portion is most typically a 2 or 3 carbon alkylene, that is ethylene or propylene. The term "alkoxy" refers to the group alkyl-O—. Such alkoxy groups include, by way of example, methoxy, ethoxy, n-propoxy, iso-propoxy, n-butoxy, tert-butoxy, sec-butoxy, n-pentoxy, n-hexoxy, 1,2-dimethylbutoxy, and the like. The term "alkoxyalkyl" refers to the group -alkylene-O-alkyl, which includes by way of example, methoxymethyl (CH$_3$OCH$_2$—), methoxyethyl (CH$_3$—O—CH$_2$—CH$_2$—) and the like. The term "alkenyl" refers to alkenyl groups preferably having from 2 to 8 carbon atoms and more preferably 2 to 6 carbon atoms and having at least 1 and preferably from 1–2 sites of alkenyl unsaturation. Such alkenyl groups include ethenyl (—CH=CH$_2$), n-propenyl (that is, allyl) (—CH$_2$—CH=CH$_2$), iso-propenyl (—C ($CH_3$)=$CH_2$), and the like. The term "alkyl" refers to monovalent alkyl groups preferably having from 1 to 8 carbon atoms and more preferably 1 to 6 carbon atoms. This term is exemplified by groups such as methyl, ethyl, n-propyl, iso-propyl, n-butyl, iso-butyl, n-hexyl, and the like. The term "aryl" refers to an unsaturated aromatic carbocyclic group of from 6 to 14 carbon atoms having a single ring (for example, phenyl) or multiple condensed rings (for example, naphthyl or anthryl). Preferred aryls include phenyl, naphthyl and the like. The term "aryloxy" refers to the group aryl-O—where the aryl group is as defined herein including optionally substituted aryl groups as also defined herein.

The term "cycloalkyl" refers to cyclic alkyl groups or cyclic alkyl rings of from 3 to 8 carbon atoms having a single cyclic ring or multiple condensed rings which can be optionally substituted with from 1 to 3 alkyl groups. Such cycloalkyl groups include, by way of example, single ring structures such as cyclopropyl, cyclobutyl, cyclopentyl, cyclooctyl, 1-methylcyclopropyl, 2-methylcyclopentyl, 2-methylcyclooctyl, and the like, or multiple ring structures such as a cycloalkyl rings include single ring structures such as cyclopentane, cyclohexane, cycloheptane, cyclooctane, and the like, or multiple ring structures. Preferred cycloalkyl rings include cyclopentane, cyclohexane, and cycloheptane.

For polyfluorene, polyquinone, polyantraquinone, polycarbazole, polyindole, polythioazole and for monomers and oligomers of the monomers of these polymers, derivatives are defined where $R_1$, $R_2$, $R_3$, $R_4$, $R_5$, $R_6$ and $R_7$ are independently selected from the group consisting of a hydrogen atom or a or a substituent, such as, for example, alkyl, alkenyl, alkoxy, cycloalkyl, cycloalkenyl, alkanoyl, alkylthio, aryloxy, hydroxy, acyl, acylamino, acyloxy, alkoxy, alkenyl, alkynyl, amino, aminoacyl, aryl, aryloxy, carboxy, carboxyalkyl, cyano, cycloalkyl, guanidino, halo, heteroaryl, heterocyclic, nitro, thiol, thioaryloxy, thioheteroaryloxy and cycloalkyl.

For poly(p-pyridine) and poly(p-pyridalvinylene) and for monomers and oligomers of the monomers of these polymers, derivatives are defined where $R_1$, $R_2$ and $R_3$ are independently selected from the group consisting of a hydrogen atom or a substituent, such as, for example, alkyl, alkenyl, alkoxy, cycloalkyl, cycloalkenyl, alkanoyl, alkylthio, aryloxy, hydroxy, acyl, acylamino, acyloxy, alkoxy, alkenyl, alkynyl, amino, aminoacyl, aryl, aryloxy, carboxy, carboxyalkyl, cyano, cycloalkyl, guanidino, halo, heteroaryl, heterocyclic, nitro, thiol, thioaryloxy, thioheteroaryloxy and cycloalkyl.

For polyaniline and for the monomer and oligomers of the monomer of this polymer, derivatives are defined where $R_1$, $R_2$, $R_3$, $R_4$, $R_5$ and $R_6$ are independently selected from the group consisting of a hydrogen atom or a substituent, such as, for example, alkyl, alkenyl, alkoxy, cycloalkyl, cycloalkenyl, alkanoyl, alkylthio, aryloxy, alkylthioalkyl, alkylaryl, arylalkyl, alkylsulfinyl, alkoxyalkyl, alkylsulfonyl, aryl, arylthio, arylsulfinyl, alkoxycarbonyl, arylsulfonyl, carboxylic acid, halogen, cyano, or alkyl substituted with one or more sulfonic acid, carboxylic acid, halogen, nitro, cyano or epoxy moieties; or any two R substituents taken together are an alkylene or alkenylene group completing a 3, 4, 5, 6 or 7 membered aromatic or alicyclic carbon ring, which ring may include one or more divalent heteroatoms of nitrogen, sulfur, sulfinyl, sulfonyl or oxygen.

For polypyrrole and for the monomer and oligomers of the monomer of this polymer, derivatives are defined where $R_1$, $R_2$ and $R_3$ are independently selected from the group consisting of a hydrogen atom or a substituent, such as, for example, alkyl, alkenyl, alkoxy, cycloalkyl, cycloalkenyl, alkanoyl, alkylthio, aryloxy, alkylthioalkyl, alkylaryl, arylalkyl, alkylsulfinyl, alkoxyalkyl, alkylsulfonyl, aryl, arylthio, arylsulfinyl, alkoxycarbonyl, arylsulfonyl, carboxylic acid, halogen, cyano, or alkyl substituted with one or more sulfonic acid, carboxylic acid, halogen, nitro, cyano or epoxy moieties; or any two R substituents taken together are an alkylene or alkenylene group completing a 3, 4, 5, 6 or 7 membered aromatic or alicyclic carbon ring, which ring may include one or more divalent heteroatoms of nitrogen, sulfure, sulfinyl, sulfonyl or oxigen.

For polythiophene, polythiophenevinylene and polyfuran and for monomers and oligomers of the monomers of these polymers, derivatives are defined where $R_1$, $R_2$, $R_3$, $R_4$, and $R_5$ are independently selected from the group consisting of a hydrogen atom or a substituent, such as, for example, alkyl, alkenyl, alkoxy, cycloalkly, cycloalkenly, alkanoyl, alkylthio, aryloxy, alkylthioalkyl, alkylaryl, arylalkyl, alkylsulfinyl, alkoxyalkyl, alkylsulfonyl, aryl, arylthio, arylsulfinyl, alkoxycarbonyl, arylsulfonyl, carboxylic acid, halogen, cyano, or alkyl substituted with one or more sulfonic acid, carboxylic acid, halogen, nitro, cyano or epoxy moieties; or any two R substituents taken together are an alkylene or alkenylene group completing a 3, 4, 5, 6 or 7 membered aromatic or alicyclic carbon ring, which ring may include one or more divalent heteroatoms of nitrogen, sulfur, sulfinyl, sulfonyl or oxygen.

For polyacetylene and for the monomer and oligomers of the monomer of this polymer, derivatives are defined where $R_1$ and $R_2$ are independently selected from the group consisting of a hydrogen atom or a subustiuent, such as, for example, alkyl, aryl, aliphatic, alkoxy, alkylthio, aryloxy or alkylthioalkyl.

FIG. 1$d$ shows examples of ionic liquids based on various monocations, while FIG. 1$e$ shows examples of ionic liquids based on polycations. The $R_1$, $R_2$, $R_3$, $R_4$, $R_5$, and $R_6$ include H; F; separate alkyl groups having from 1 to 10 carbon atoms or joined together to constitute unitary alkylene radicals having from 2 to 4 carbon atoms thereby forming a ring structure; separate phenyl groups; and substituted alkyl groups, alkylene radicals or phenyl groups. $A_1$ and $A_2$ include alkylene groups and substituted alkylene groups. The anion $X^-$ includes, but is not limited to, $F^-$; $Cl^-$; $Br^-$; I; $BF_4^-$; $NO_3^-$; $ClO_4^-$; $PF_6^-$; $N(CN)_2^-$; $RSO_3^-$; and $RCOO^-$ where R is an alkyl group; substituted alkyl group; phenyl group; $(CF_3)_2PF_4^-$, $(CF_3)_3PF_3^-$; $(CF_3)_4PF_2^-$; $(CF_3)_5PF^-$; $(CF_3)_6P^-$; $(CF_2SO_3^-)_2$; $(CF_2CF_2SO_3^-)_2$; $(CF_3SO_2)_2N^-$; $CF_3CF_2(CF_3)_2CO^-$; $(CF_3SO_2)_2CH^-$; $(SF_5)_3C^-$; $(CF_3SO_2SO_2)_3C^-$; $[O(CF_3)_2C_2(CF_3)_2O]_2PO^-$; or $CF_3(CF_2)_7 SO_3^-$.

A. Electrochemical Synthesis of Conjugated Polymers in Ionic Liquids

Figure 2:
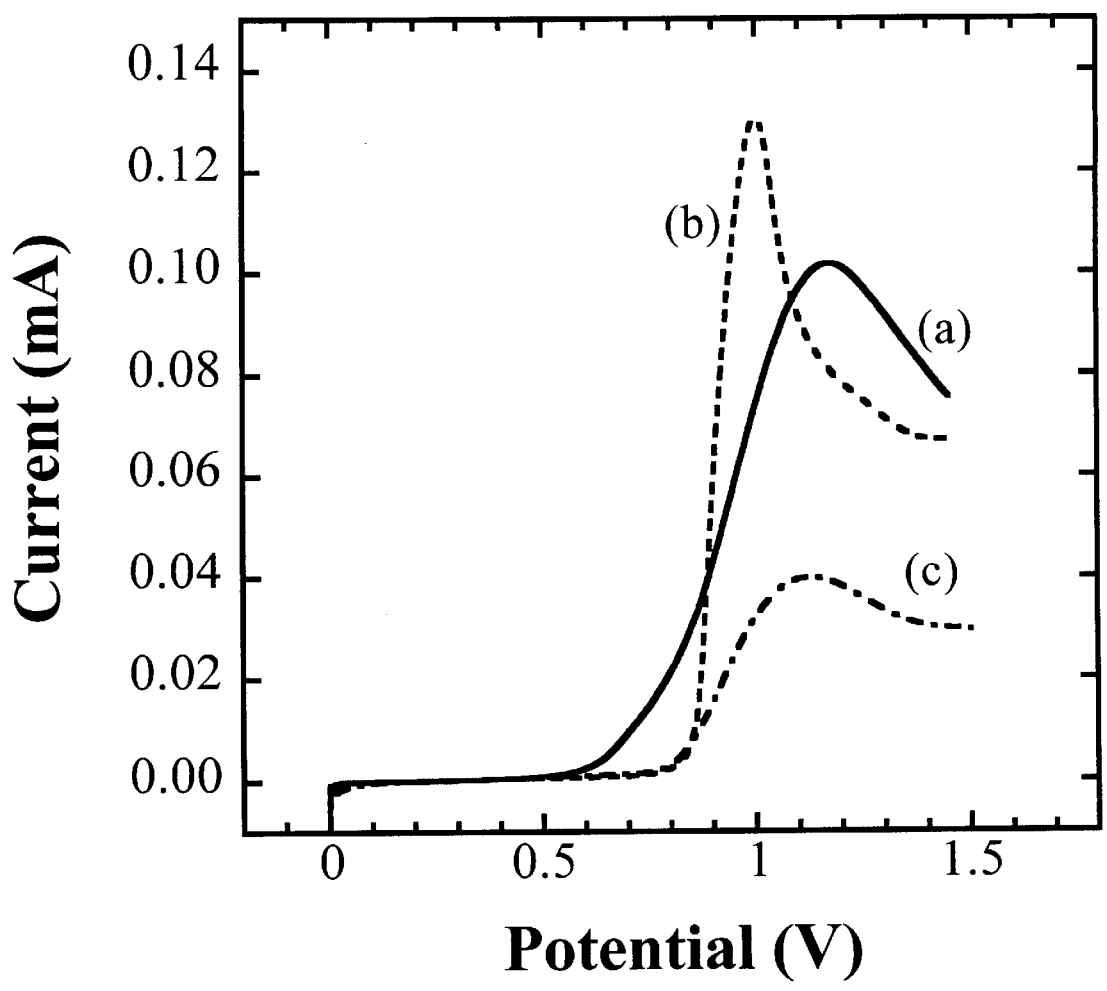
FIG. 2 shows the oxidation of monomers at a platinum disc electrode (S=0.018 $cm^2$) of: (a) 0.1M pyrrole in [BMIM][$BF_4$], where BMIM is 1-butyl-3-methylimidazolium; (b) 0.1 M 3,4-ethylenedioxythiophene in [BMIM][$BF_4$]; and (c) 0.5M aniline and 2 M $CF_3COOH$ in [BMIM][$BF_4$], all at a scan rate of 50 mV/s.

Three typical conjugated polymers, namely polypyrrole (PPy), poly(3,4-ethylenedioxythiophene) (PEDOT) and polyaniline (PANI) were prepared from the corresponding monomer-containing ionic liquids. For the preparation of PPy and PEDOT, the polymerization solution contained only the monomer and an ionic liquid. However, for the preparation of PANI, an acid is required to ensure deposition of the polymer and an electroactivity thereof similar to that reported previously for other organic electrolyte systems (See, e.g., T. Osaka et al., *J. Electrochem. Soc.* 138, 2853. (1991)). In order to ensure the exclusion of water, organic acids, such as $CF_3COOH$, were used rather than aqueous acids. Conjugated polymers can be deposited onto metal electrodes, such as platinum (Pt) and gold (Au) as examples, and ITO (Indium Tin Oxide)-coated glass electrodes. The oxidation of monomers at a Pt electrode in ionic liquids is illustrated in FIG. 2 hereof which shows the oxidation of monomers at a platinum disc electrode (S=0.018 cm$^2$) of: (a) 0.1M pyrrole in [BMIM][BF$_4$], where BMIM is 1-butyl-3-methylimidazolium; (b) 0.1 M 3,4-ethylenedioxythiophene in [BMIM][BF$_4$]; and (c) 0.5M aniline and 2 M CF$_3$COOH in [BMIM][BF$_4$], all at a scan rate of 50 mV/s in an electrochemical cell which includes the platinum disc as the working electrode, a 1.5 mm diameter platinum wire as the counter electrode and a 1.0 mm diameter silver wire as the reference electrode. Oxidation of pyrrole, 3,4-ethylenedioxythiophene and aniline began at 0.50 V, 0.80 V and 0.80 V, respectively.

Figure 3A:
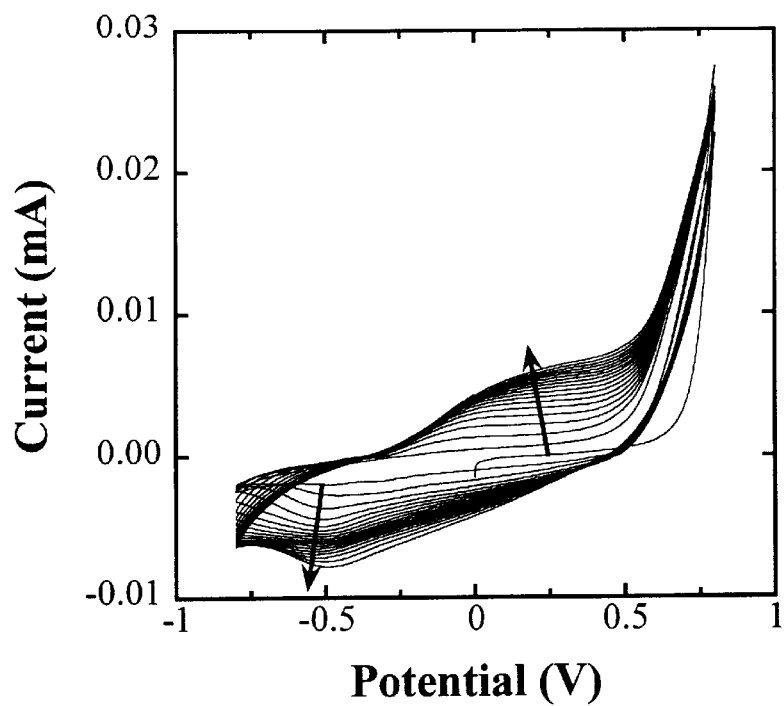
FIG. 3a, FIG. 3b and FIG. 3c are cyclic voltammograms obtained at a platinum disc electrode (S=0.018 $cm^2$) in 0.1 M pyrrole in [BMIM][$BF_4$]; 0.1M 3,4-ethylenedioxythiophene in [BMIM][$BF_4$]; and 0.5M aniline and 2 M $CF_3COOH$ in [BMIM][$BF_4$], respectively, all at a scan rate of 50 mV/s.
Figure 3B:
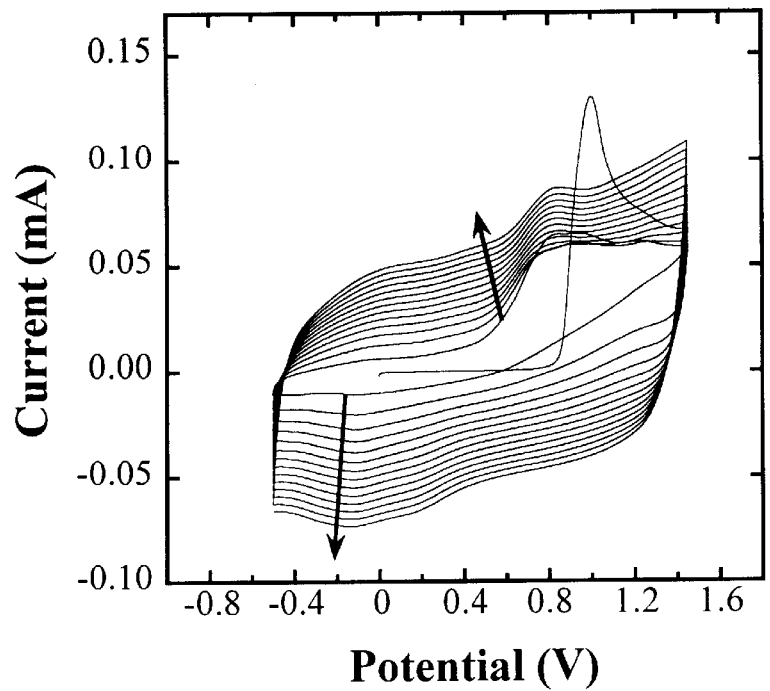
Figure 3C:
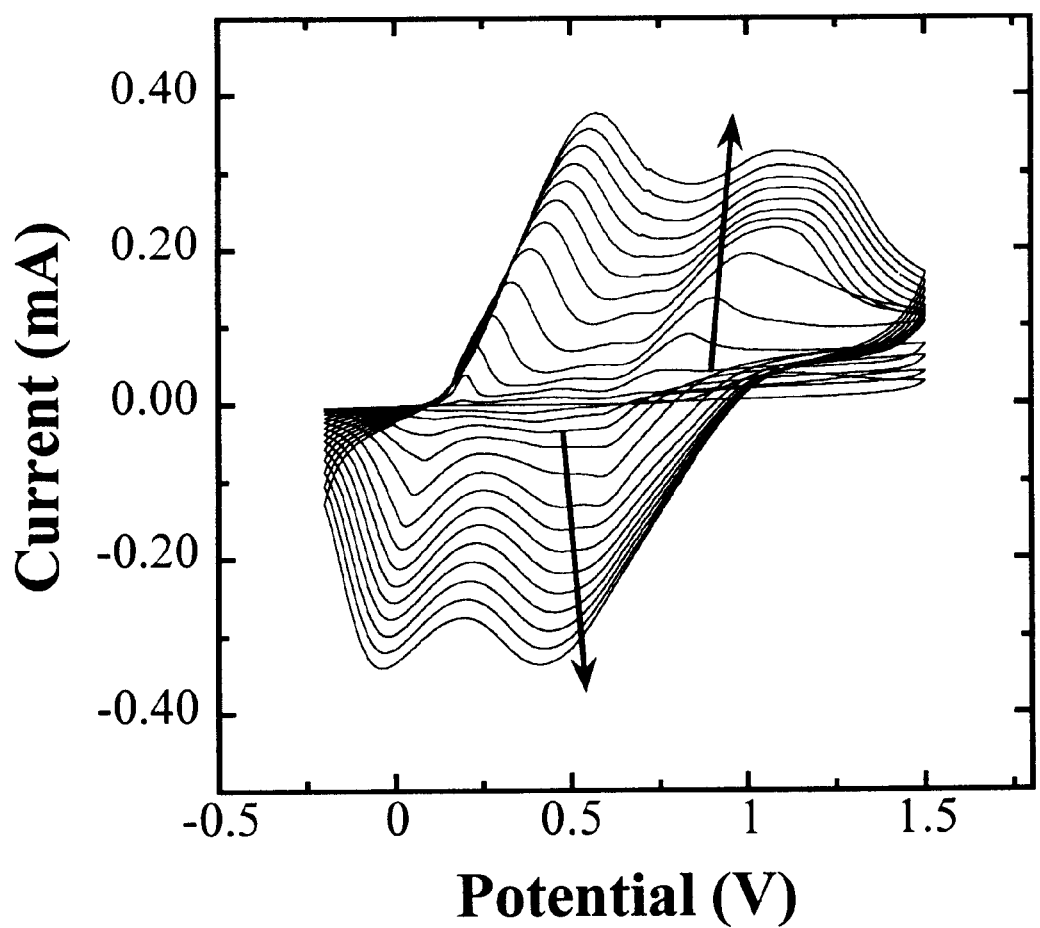

Electrochemical synthesis of conjugated polymers in ionic liquids can be achieved using three methods: (1) potentiodynamic; (2) potentiostatic; and (3) galvanostatic. The electrochemical cell and the polymerization solutions used were the same as those set forth hereinabove. FIG. 3 hereof illustrates the results using the potentiodynamic method. FIG. 3a, FIG. 3b and FIG. 3c are cyclic voltammograms obtained at a platinum disc electrode (S=0.018 cm$^2$) in 0.1 M pyrrole in [BMIM][BF$_4$]; 0.1M 3,4-ethylenedioxythiophene in [BMIM][BF$_4$]; and 0.5M aniline and 2 M CF$_3$COOH in [BMIM][BF$_4$], respectively, all at a scan rate of 50 mV/s. The increased currents upon cycling the potential are illustrated by arrows in FIG. 3 and indicate the deposition of electroactive conjugated polymers onto the substrate Pt electrodes. Cycle numbers for polymerization were 18 for PPy, 14 for PDOT and 15 for PANI which resulted in a polymer thickness of approximately 0.5 μm for all polymer films prepared in this manner.

Figure 4A:
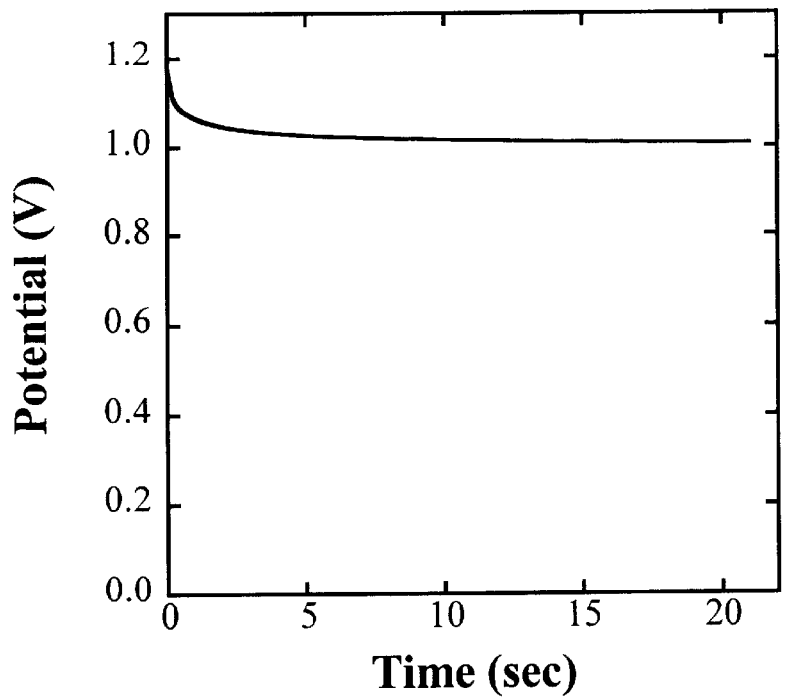
FIG. 4a and FIG. 4b are chronopotentiograms obtained at 7 electrically connected ITO-coated glass pixels (7×0.25 cm×1.7 cm) used for the deposition of PEDOT, and at 1 ITO-coated glass pixel (0.25 cm×1.7 cm) used for the deposition of PANI, respectively, in 0.5M EDOT in [BMIM][$BF_4$] for PEDOT and 0.5M aniline and 2 M $CF_3COOH$ in [BMIM][$BF_4$] for PANI, both with a current density of 0.5 $mA/cm^2$.
Figure 4B:
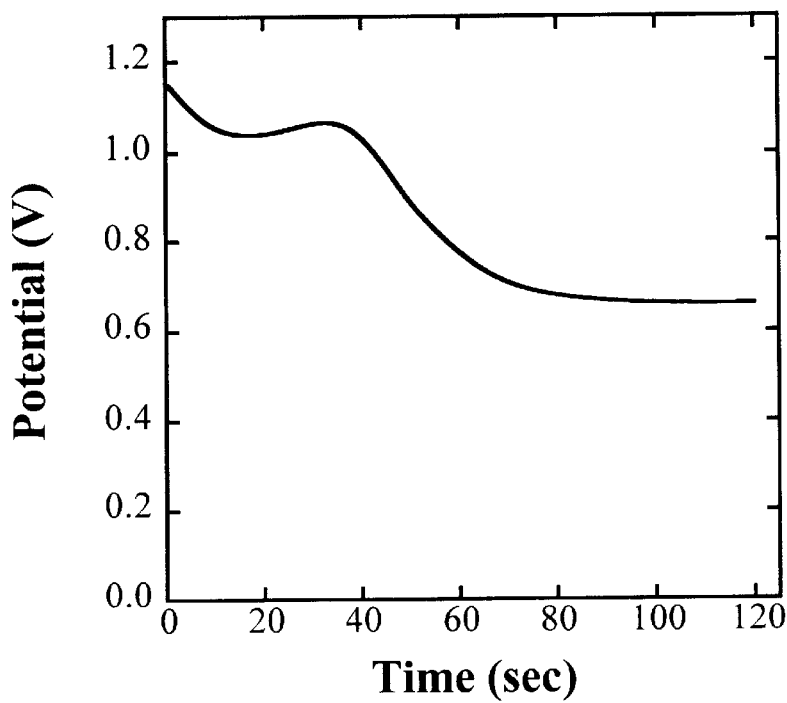

FIG. 4 hereof illustrates the results using a galvanostatic synthesis. FIG. 4a and FIG. 4b are chronopotentiograms obtained at 7 electrically connected ITO-coated glass pixels (7×0.25 cm×1.7 cm) used for the deposition of PEDOT, and at 1 ITO-coated glass pixel (0.25 cm×1.7 cm) used for the deposition of PANI, respectively, in 0.5M PEDOT in [BMIM][BF$_4$] for PEDOT and 0.5M aniline and 2 M CF$_3$COOH in [BMIM][BF$_4$] for PANI, both with a current density of 0.5 mA/cm$^2$. The low, constant potentials of 1.05 V for PEDOT and 0.70 V for PANI, respectively, occurring sometime after the current was first applied indicate the deposition of electroactive conjugated polymers onto the substrate ITO-coated glass electrodes. Deposition times for PEDOT and PANI were 40 s and 120 s, respectively, resulting in a thickness of approximately 0.08 μm for PEDOT and 0.2 μm for PANI.

B. Electroactivity of Conjugated Polymers in Ionic Liquids

Figure 5:
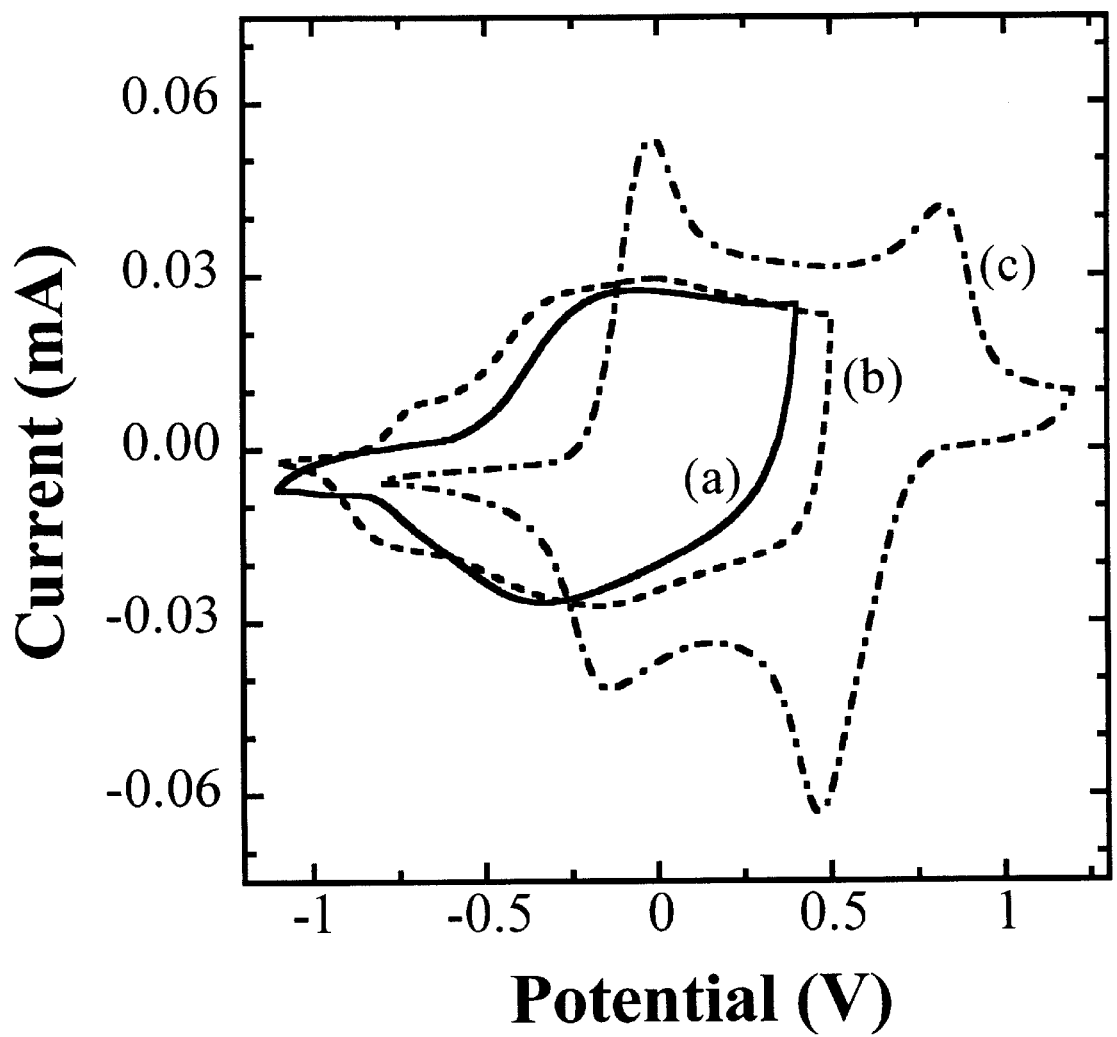
FIG. 5 shows cyclic voltammograms of conjugated-polymer coated platinum electrodes obtained in [BMIM][$BF_4$] for: (a) PPy; (b) PEDOT; and (c) PANI, all at a scan rate of 50 mV/s, where the conjugated polymers were prepared in [BMIM][$BF_4$] as in a similar manner to that described in FIG. 3 hereof.

Conjugated polymers electrochemically synthesized in ionic liquids in accordance with the teachings of the present invention showed electroactivity in the ionic liquids. See FIG. 5 hereof, where cyclic voltammograms are shown for conjugated-polymer coated platinum electrodes obtained in [BMIM][BF$_4$] for: (a) PPy; (b) PEDOT; and (c) PANI, all at a scan rate of 50 mV/s in an electrochemical cell which included a polymer-coated platinum disc electrode as the working electrode, a 1.5 mm diameter platinum wire as the counter electrode and a 1.0 mm diameter silver wire as the reference electrode. The conjugated polymers were prepared in [BMIM][BF$_4$] as in a similar manner to that described for FIG. 3 hereof. The typical shapes of cyclic voltammetric peaks obtained for these polymers are similar to those reported previously by others for other electrolyte systems. Stable cyclic voltammograms were obtained for all polymers after potential cycling.

Emphasis should be placed on the stability of polyaniline in ionic liquids. Upon potential cycling in the potential range up to 1.2 V which covers the entire redox process for polyaniline (lucoemeraldine←→emeraldine←→pernigraniline), no middle peak and thus no degradation was observed. By contrast, in aqueous acidic electrolytes (See, e.g., T. Kobayashi et al., *J. Electroanal. Chem.* 161, 419 (1984)), a typical middle peak appears between the two original peaks if the potential is scanned to that appropriate for the pernigraniline oxidation state for several cycles. As the number of cycles is increased, this middle peak gradually increases while the original two peaks decrease, resulting in the ultimate degradation of the polyaniline. Thus, the use of ionic liquids as electrolytes for the synthesis and generation of electroactivity of polyaniline ensures the long-term stability of the resulting polymer.

Previously, in order to avoid the problems encountered with aqueous electrolytes, polyaniline was prepared in organic electrolytes such as propylene carbonate and acetonitrile. However, due to the evaporation of solvent and the absorption of moisture, it was found that the polymer was required to be prepared in a dry glove box in order to ensure a long lifetime therefor.

C. Electrochroism of Conjugated Polymers in Ionic Liquids

Using the same procedures used to generate FIG. 3 and FIG. 4 hereof, PPy, PEDOT and PANI were deposited on ITO-coated glass electrodes. The reversible color changes of these conjugated polymers (PPy: brown←→blue; PEDOT: sky blue tint←→dark blue; and PANI: transparent yellow←→green←→dark blue) between their oxidized and reduced states has been achieved in ionic liquids. These color changes are similar to those reported using other electrolyte systems.

D. Stable Electrochromic Performance of Polyaniline in Ionic Liquids

Figure 6:
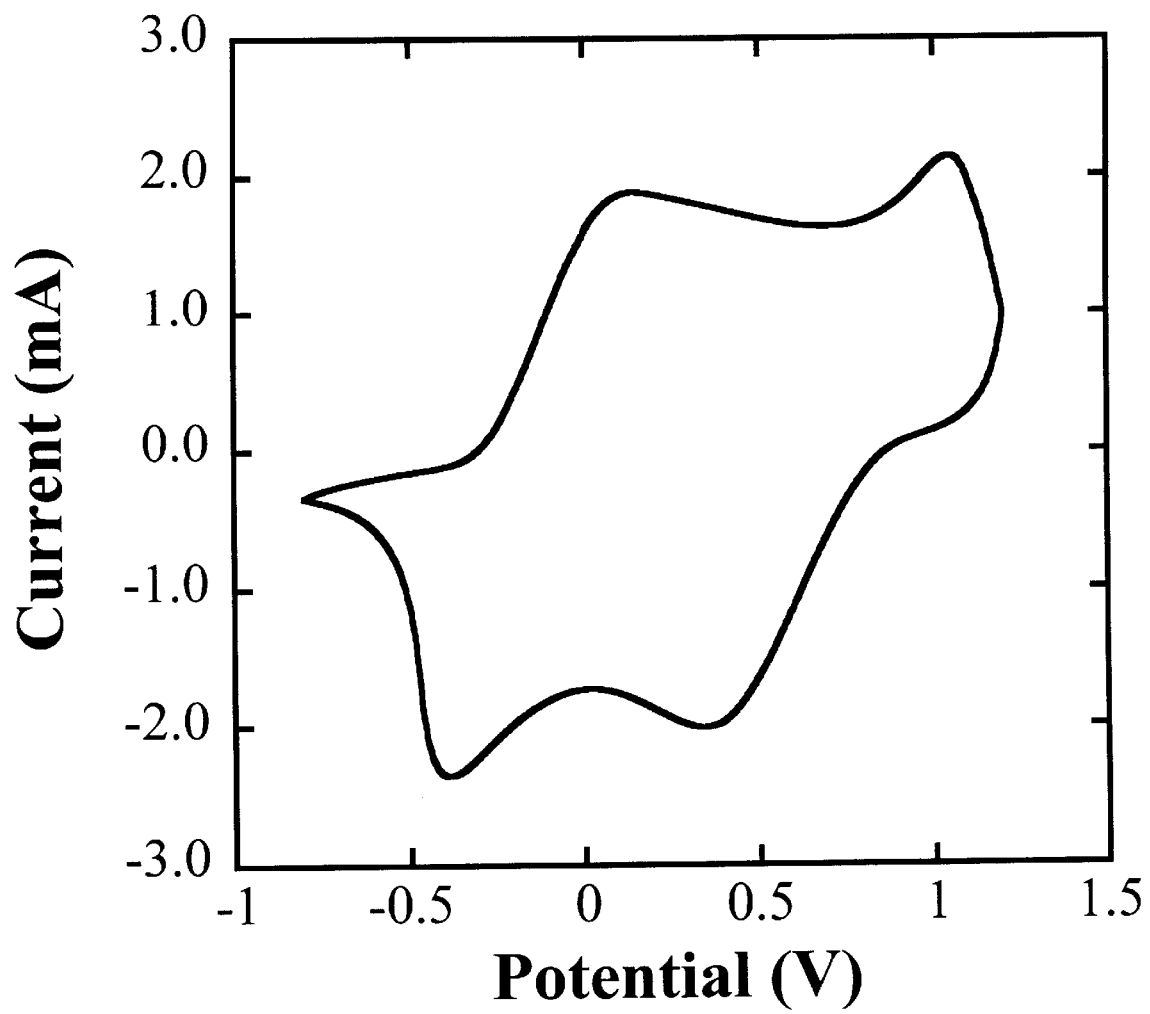
FIG. 6 is a cyclic voltammogram of a PANI-coated, ITO-coated glass electrode obtained in [BMIM][$BF_4$] with a scan rate of 50 mV/s, where the surface area of the ITO-coated glass electrode is 0.7 cm×4.2 cm, and the PANI was coated onto the ITO-coated glass electrode as described in FIG. 3.

Polyaniline was deposited electrochemically onto an ITO-coated glass electrode as described in the discussion for FIG. 3 hereof. The electroactivity of the PANI-coated ITO-coated electrode was explored in [BMIM][BF$_4$], where BMIM is 1-butyl-3-methylimidazolium, using cyclic voltammetry and the same procedure as set forth in the discussion of FIG. 5 hereof. Upon potential cycling, two pairs of peaks associated with the typical multiple redox processes of polyaniline were obtained as shown in FIG. 6 hereof which shows a cyclic voltammogram of a PANI-coated, ITO-coated glass electrode obtained in [BMIM][BF$_4$] with a scan rate of 50 mV/s. The surface area of the ITO-coated glass electrode is 0.7 cm×4.2 cm.

Continued potential cycling did not cause polymer degradation with the appearance of a middle peak between the original two pairs of peaks, which is a common indicator of the degradation of polyaniline in aqueous electrolytes.

Figure 7:
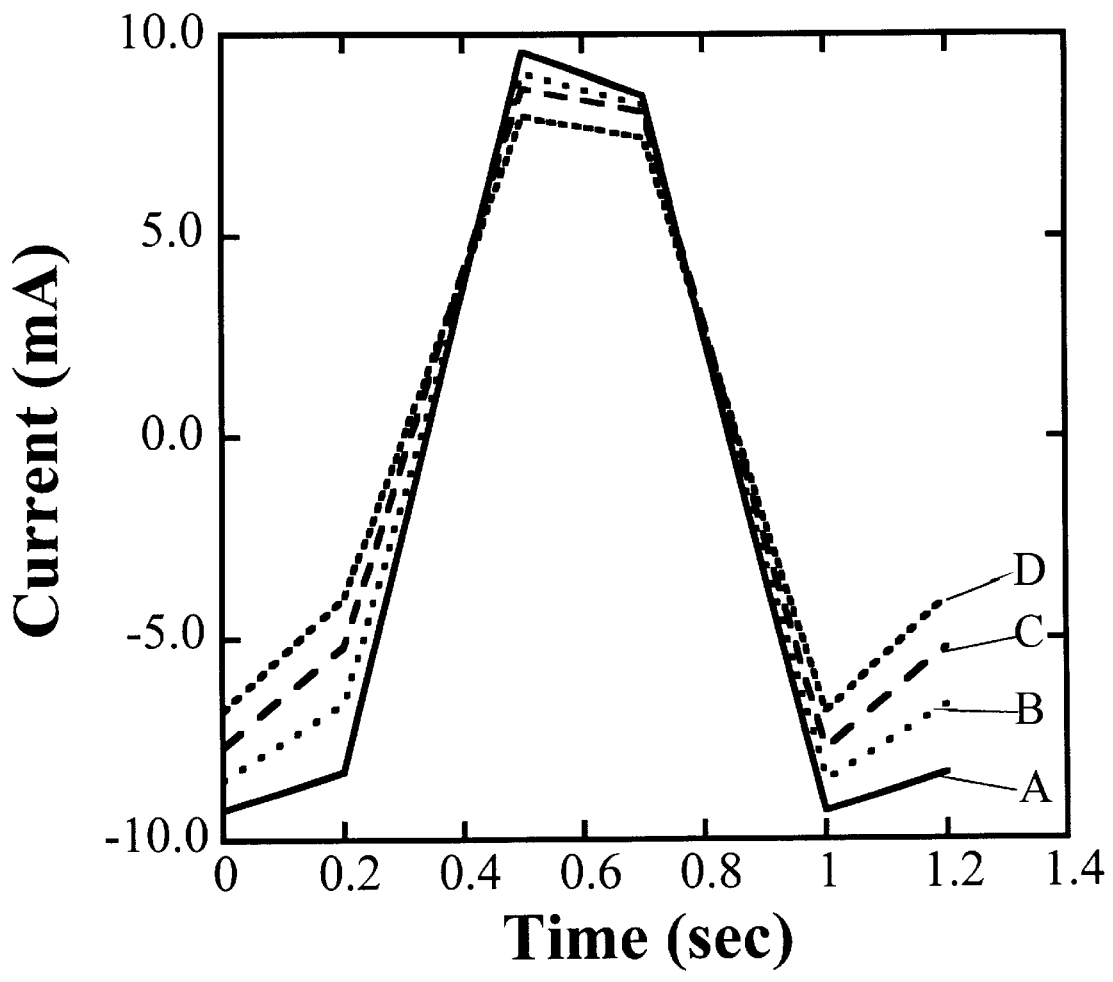
FIG. 7 shows chronoamperograms taken at different numbers of cycles in [BMIM][BF$_4$] for the PANI-coated, ITO-coated glass electrode used in FIG. 6 hereof, where the potential switching was performed between −0.6 V and +1.1 V with a pulse width of 0.5 s, and curve A is the 3$^{rd}$ cycle; curve B is the 330,000$^{th}$ cycle; curve C is the 630,000$^{th}$ cycle; and curve D is the 1,000,000$^{th}$ cycle.

Lifetime tests were performed in the same ionic liquid in air by potential switching between −0.6 V and +1.1 V (which spans the entire redox process for polyaniline) with a pulse width of 0.5 s. A color change between transparent yellow and dark blue was obtained upon switching between these two potentials. Current responses at different cycles during the lifetime test were recorded and are illustrated in FIG. 7 hereof which shows chronoamperograms taken at different numbers of cycles in [BMIM][BF$_4$] for the PANI-coated, ITO-coated glass electrode used in FIG. 6 hereof. Curve A shows the 3$^{rd}$ cycle; curve B the 330,000$^{th}$ cycle; curve C the 630,000$^{th}$ cycle; and curve D the 1,000,000$^{th}$ cycle.

No significant decay in electroactivity or coloration was observed after the continuous switching for 1,000,000 cycles between the fully reduced and fully oxidized states of the PANI coated ITO-coated glass electrode.

E. Comparison of Electrochromic Performance of Polyaniline in Other Electrolytes Polyaniline is one of the most frequently studied electrochromic materials. Its electrochroism has been extensively investigated previously in aqueous electrolyte (See e.g., T. Kobayashi et al., *J. Electroanal Chem.* 161, 419 (1984) and T. Kobayashi et al., *J. Electroanal Chem.* 177, 281.(1984)). However, due to the observed degradation of polyaniline upon potential scanning to the second redox state (emeraldine←→pernigraniline), the potential range had to be narrowed to the first redox state (lucoemeraldine←→emeraldine) which results in a poor coloration contrast (between transparent yellow and green, rather than to dark blue). Moreover, although a lifetime as high as 1 million cycles has been reported in this narrow potential range, evaporation of the aqueous electrolytes limits the practical applications of the aqueous system in the fabrication of solid-state devices.

In order to overcome the problems of aqueous electrolytes, polyaniline electrochromic phenomena have been investigated in organic liquid electrolytes such as PC-LiClO$_4$ (See e.g., T. Asaoka et al., 40$^{th}$ ISE Meeting (Kyoto), Ext. Abs., I, 245-6 (1989)). Therein it is stated that the switching potential range can be extended to the second redox state with a color change from transparent-colorless to dark blue. Greater color contrast in organic liquid media is an advantage in practical applications. However, reported cyclic voltammetry testing only involved 100 cycles of operation without observable degradation. Osteryoung et al. reported a lifetime of $3\times10^4$ cycles for polyaniline in Lewis acid containing ionic liquid AlCl$_3$-IMCl systems (See, e.g., J. Tang and R. A. Osteryoung, supra). However, this was performed in a narrow potential range covering only the first redox process of polyaniline (lucoemeraldine←→emeraldine) which, as stated, limits the coloration contrast of polyaniline.

In accordance with the present invention, long lifetime has been obtained in the potential range covering the entire redox process of polyaniline (lucoemeraldine←→emeraldine←→pernigraniline), ensuring high coloration contrast for polyaniline as a good candidate of electrochromic material.

F. Fabrication of Solid-state Conjugated Polymer Electrochromic Direct Addressing Displays with Ionic Liquids as Electrolytes In accordance with the teachings of the present invention, ionic-liquid-based conjugated polymer electrochromic displays were realized in two types: direct addressing displays, and multiplex addressing displays. In a direct addressing display, each pixel is driven directly. In a multiplex addressing display, pixels are arranged into a matrix and addressed by their row and column. When the number of pixels is low, such as for alphanumeric displays, direct addressing is convenient and economical. However, if a large number of pixels are required, such as for high-resolution monitors, direct addressing becomes difficult, and multiplex addressing is necessary. As an example, for a display matrix having "a" rows and "b" columns, a×b drivers are needed for direct addressing, while only a+b drivers needed for multiplex addressing.

To fabricate solid-state conjugated polymer electrochromic devices in accordance with the teachings of the present invention, two polymer-coated electrodes are required: an anodically coloring polymer, and a cathodically coloring polymer. As an example, polyaniline (PANI) and poly(3,4-ethylenedioxythiophene) (PEDOT) were employed as anodically and cathodically coloring polymers, respectively. Both polymers were electrochemically deposited onto patterned ITO-coated glass electrodes from ionic liquids as discussed in the procedure set forth for FIG. 4 hereinabove. The present polymer electrodes can be used directly for device fabrication without the necessity for a drying process as is commonly employed for polymers synthesized in aqueous electrolytes.

Figure 8:
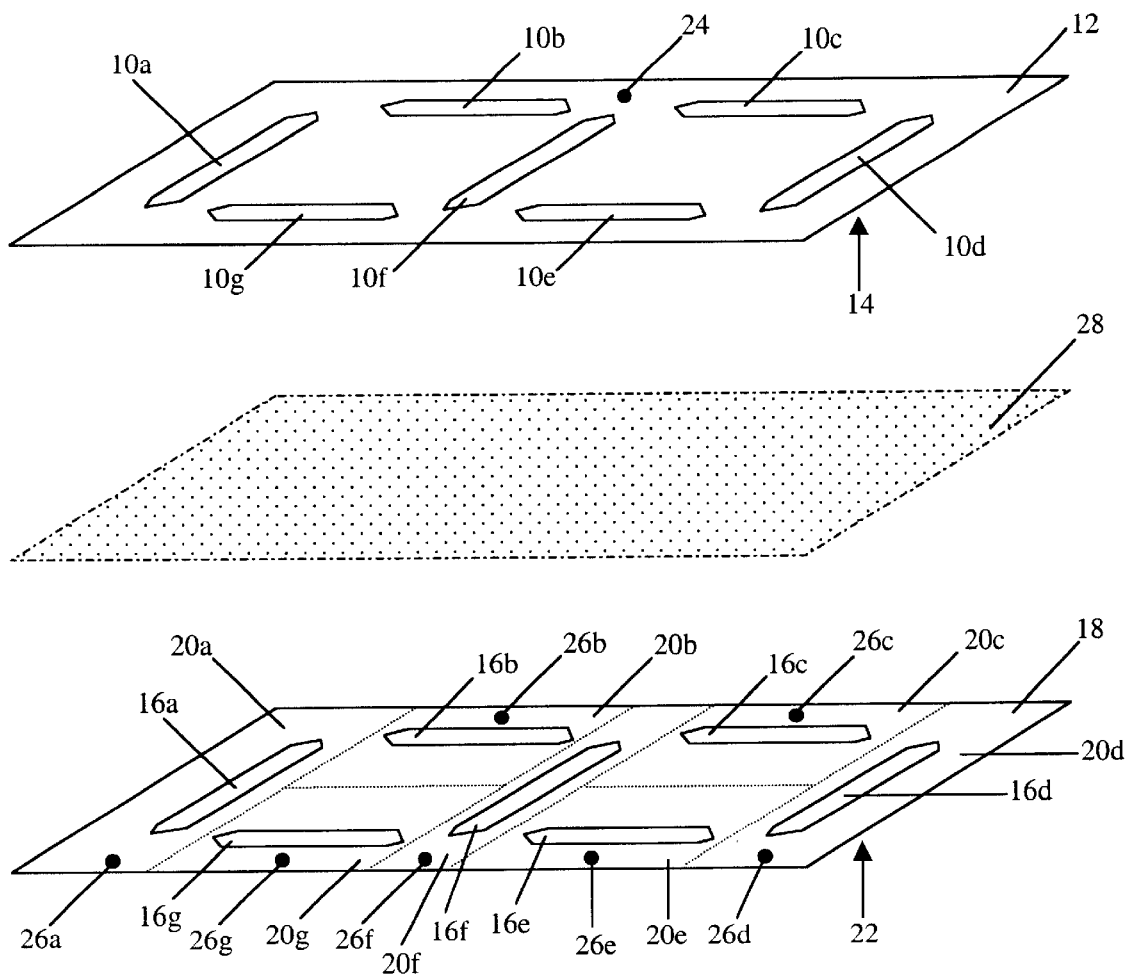
FIG. 8 is a schematic representation of a direct-addressing electrochromic display where an anodically coloring conjugated polymer is coated onto a patterned ITO-coated glass electrode, and a cathodically coloring conjugated polymer is coated onto a patterned ITO-coated glass electrode, the two electrodes being spaced apart and in electrical contact with an ionic liquid therebetween as the electrolyte.

A typical structure for a conjugated polymer direct addressing electrochromic display incorporating ionic liquids as electrolytes is shown in FIG. 8 hereof. Seven strips of PEDOT, 10a–10g, are generated onto an unsegmented ITO-coated glass plate, 12, forming the cathode, 14, while seven PANI strips, 16a–16g, one strip opposing each PEDOT strip 10a–10g are generated onto a segmented ITO-coated glass plate, 18, one per segment, 20a–20g, forming the anode, 22. One electrical contact, 24, is made with the cathode, while 7 electrical contacts, 26a–26g, are made with the anode, one contact for each ITO-coated glass plate segment. The two polymer electrodes are separated by a thin layer of ionic liquid electrolyte, 28, having a thickness of approximately 100 μm. The edges of the device were sealed using epoxy resin. Joint electrical contact for PEDOT and independent electrical contacts for PANI were made by attaching metal wires using silver paint. Due to the higher viscosity of ionic liquids than that for aqueous or other non-aqueous electrolytes, ionic liquids can be used directly without the introduction of a gel or polymer system. The absence of gel/polymer in the electrolyte achieves higher conductivity and faster ion movement which leads to high performance devices having lower operating voltages and increased speed for coloration changes.

In actual operation, all 7 pixels 10a–10g of PEDOT coated ITO-coated glass electrodes were used as a joint counter electrode, 14. Each pixel of PANI 16a–16g coated onto the segmented ITO-coated glass electrode was used as a separate working electrode 22. The separate electrical contacts on each PANI pixel permitted independent voltages to be established between each PANI pixel and the joint, PEDOT coated ITO-coated glass counter electrode. Clearly, any number of pixels may be used.

Figure 9:
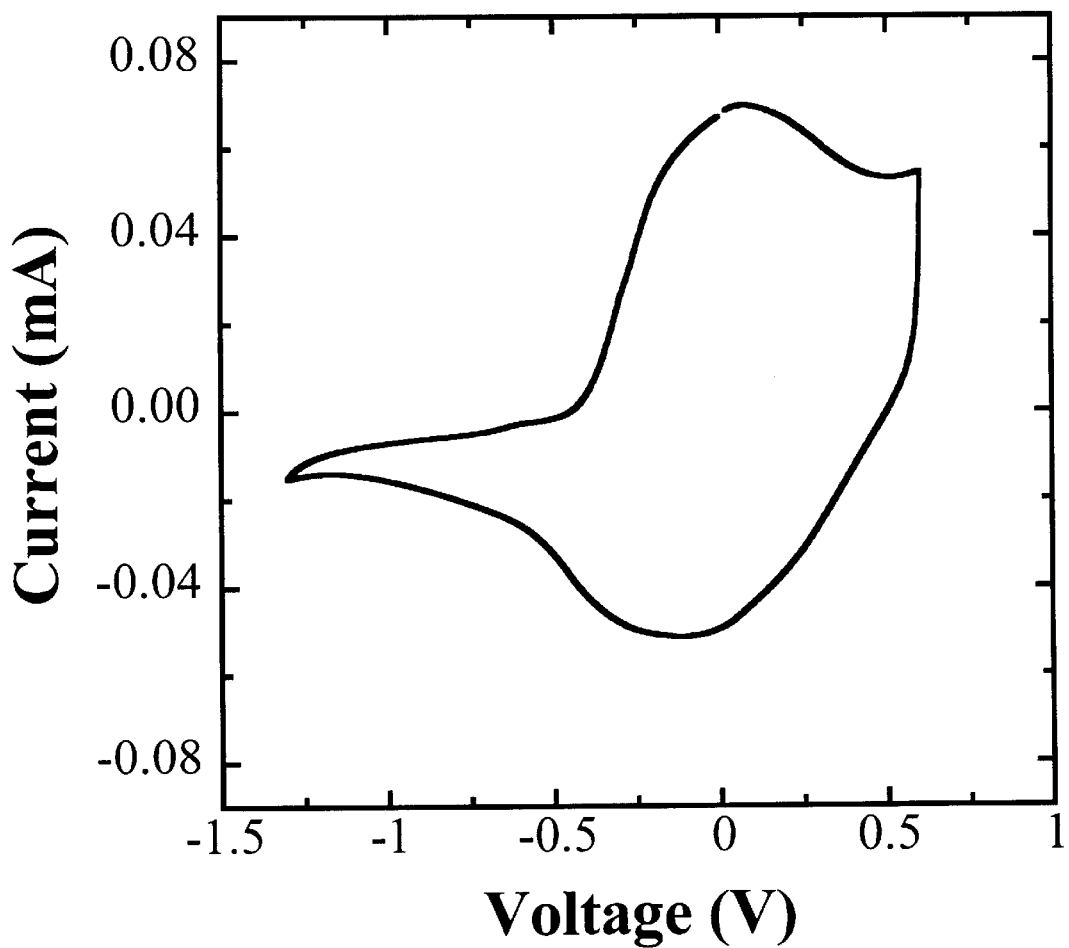
FIG. 9 is a cyclic voltammogram obtained for a direct-addressing electrochromic display which includes one pixel of PANI-coated, patterned ITO-coated glass as the working electrode and a PEDOT-coated, patterned ITO-coated glass counter electrode having 7-pixels in electrical connection, both electrodes being in electrical contact with the ionic liquid [BMIM][BF$_4$] as the electrolyte, where the surface area of each ITO-coated glass electrode pixel is 0.25 cm×1.7 cm.

Cycling voltage for a pair consisting of a pixel of PANI coated ITO-coated glass working electrode and the joint PEDOT coated ITO-coated glass counter electrode resulted in a well-defined cyclic voltammogram as shown in FIG. 9 hereof, indicating the well-defined redox process for the combination of PANI as anodically coloring polymer, PEDOT as cathodically coloring polymer and ionic liquid [BMIM][BF$_4$] as electrolyte and thus the appropriate construction of the device. In FIG. 9, the surface area of each ITO-coated glass electrode pixel is 0.25 cm×1.7 cm.

Figure 10:
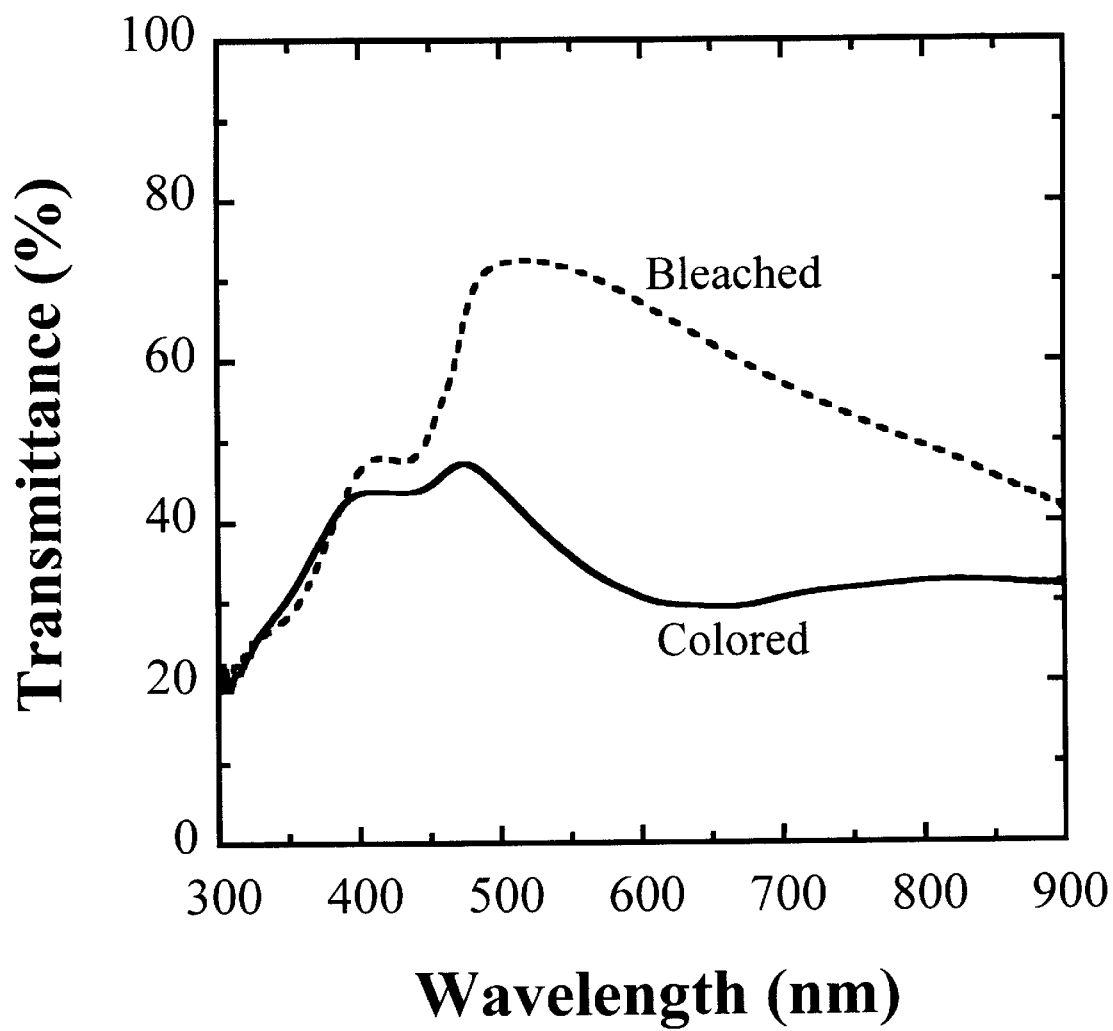
FIG. 10 shows UV-Vis spectra of one pixel for the electrochromic display used in FIG. 9 for the bleached state thereof at −1.3 V and the colored state thereof at +0.6 V.

UV-Vis spectra for this same pixel obtained for the bleached (light green) and colored (black) states are shown in FIG. 10. The bleached state occurs at −1.3 V, while the colored state occurs at +0.6 V. The maximum contrast was between 620 nm and 670 nm, with a Δ%T of 35%. This value is slightly higher than that for a similar electrochromic device using PANI as the anodically coloring polymer and PEDOT as the cathodically coloring polymer and water containing poly(2-acrylamido-methane-2-propanesulfonicacid) as the electrolyte (See e.g., D. DeLongchamp and P. T. Hammond, *Adv. Mater.* 13, 1455 (2001)).

Figure 11:
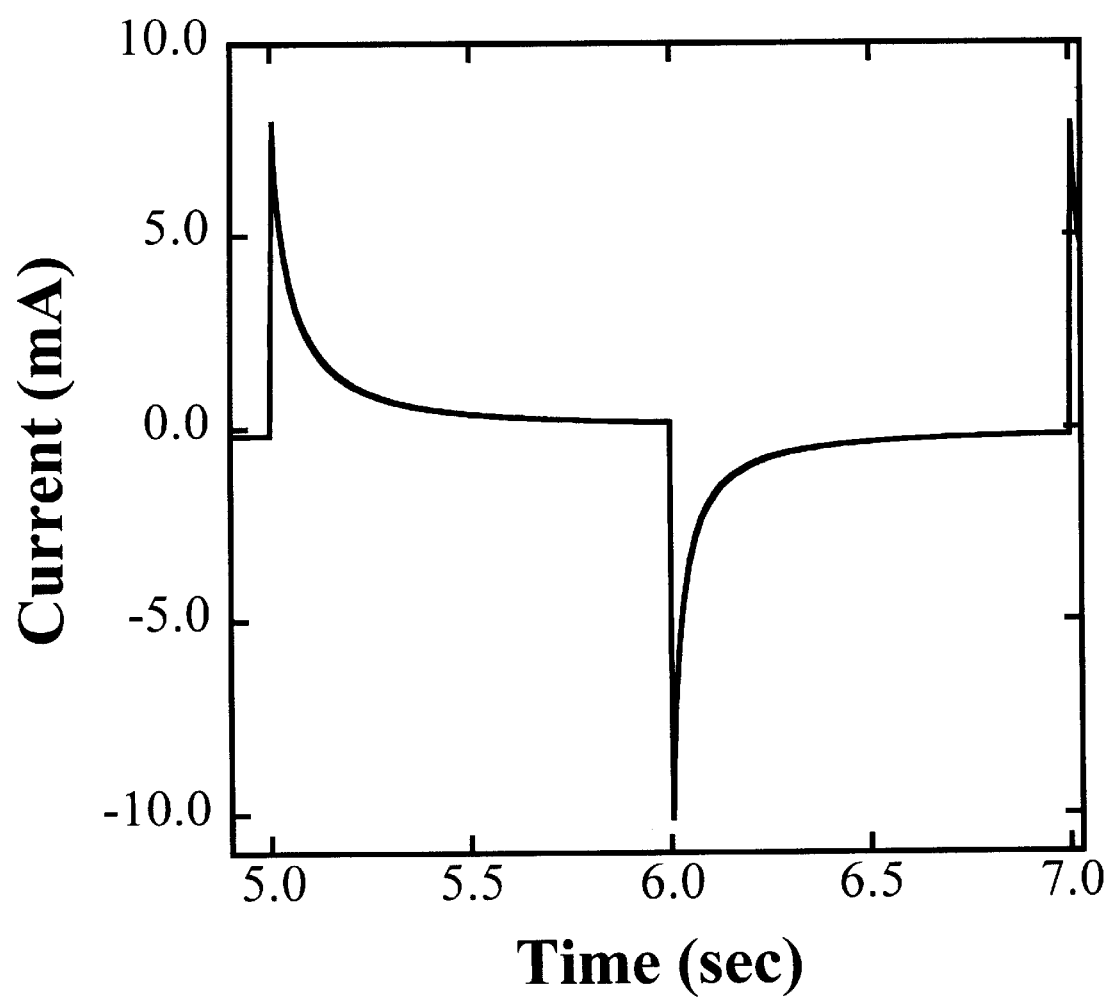
FIG. 11 is a chronoamperogram of one pixel obtained for the electrochromic display used in FIG. 9 hereof where the voltage was switched between −1.3 V and +0.6 V with a pulse width of 1 s.

Chronoamperogram for the same pair pixel obtained upon voltage switching between the bleached (−1.3 V) and colored (+0.6 V) states with the pulse width of 1 s is shown in FIG. 11. Rapid decay in current response upon voltage switching indicated the fast redox process and thus the rapid attainment of the coloration and bleaching states of the device. Coulombic efficiency, defined by the ratio of injected charge ($Q^+$) upon coloring to removed charge ($Q^-$) upon bleaching, was determined as 98%, indicating good reversibility in redox process and coloration of the device. Switching the same pair pixel with shorter pulse widths (higher frequencies) resulted in decreased currents as would be expected. Exemplary current responses upon coloring at +0.6 V with different pulse widths are summarized in the TABLE. Full color change was observed at the switching frequency up to 5 Hz. At higher frequencies (up to 20 Hz), 67% of electroactivity was still observed by comparing the current with that obtained at 1 Hz. This again confirmed the fast redox process and coloration of the device.

TABLE

Current response for one pixel pair at +0.6 V and various frequencies.

| Voltage Pulse Width (sec) | Frequency (Hz) | Current (mA) | Remaining electroactivity (%) |
|---|---|---|---|
| 1 | 1 | 7.97 | 100 |
| 0.5 | 2 | 7.30 | 92 |
| 0.2 | 5 | 5.89 | 74 |
| 0.1 | 10 | 5.58 | 70 |
| 0.05 | 20 | 5.33 | 67 |

Figure 12:
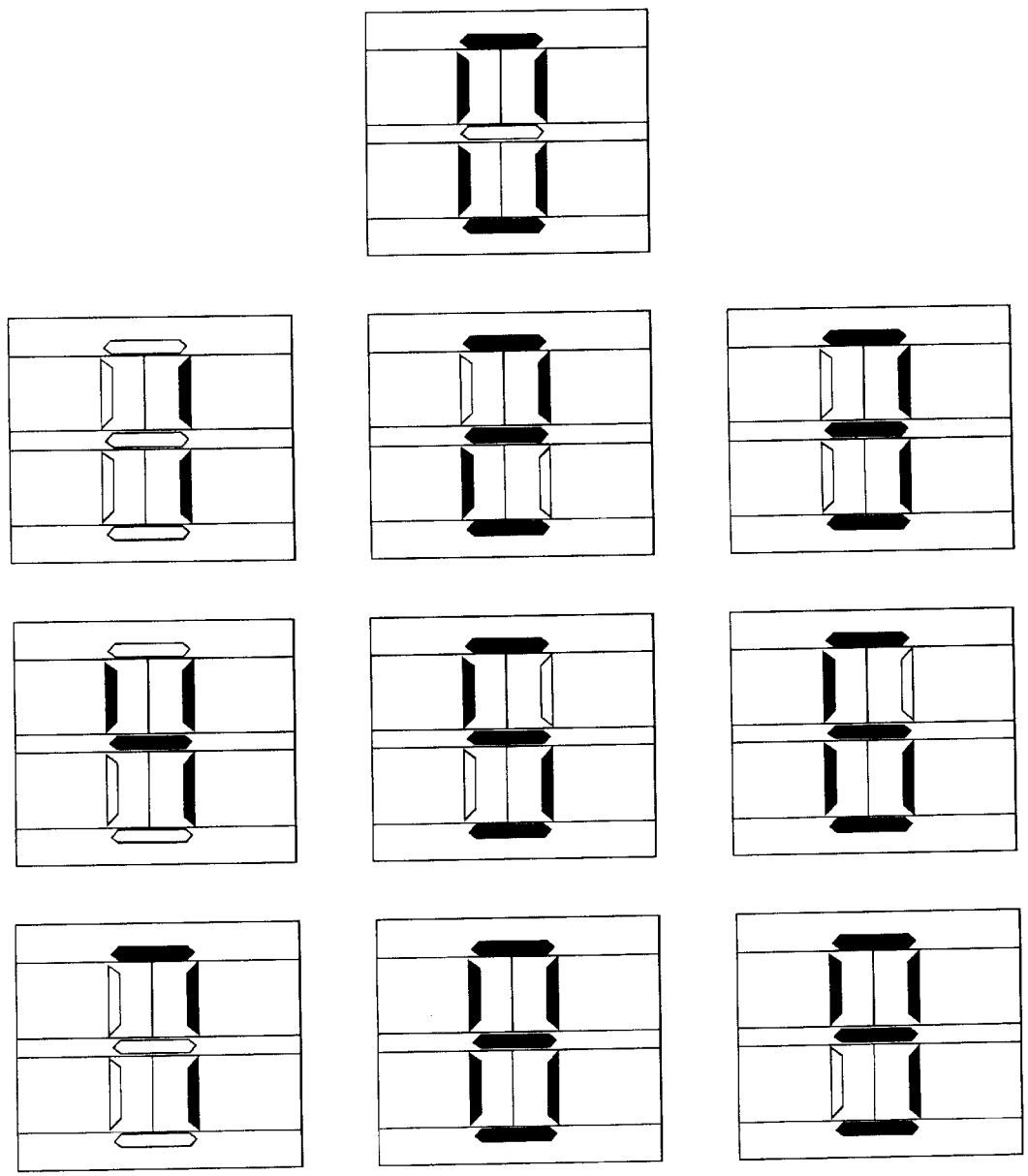
FIG. 12 shows the alphanumeric output from the display device described in FIG. 8 hereof when chosen pixels are addressed by applying voltage to them.

Using a controller powered by a 9V battery to apply voltages to the appropriate pixels, alphanumeric numbers from 0 to 9 were observed using the apparatus described in FIG. 8 hereof as shown in FIG. 12. Distinguishable alphanumeric output was obtained up to 5 Hz, and the rapid flashing color change could be seen at frequencies up to 20 Hz.

Figure 13:
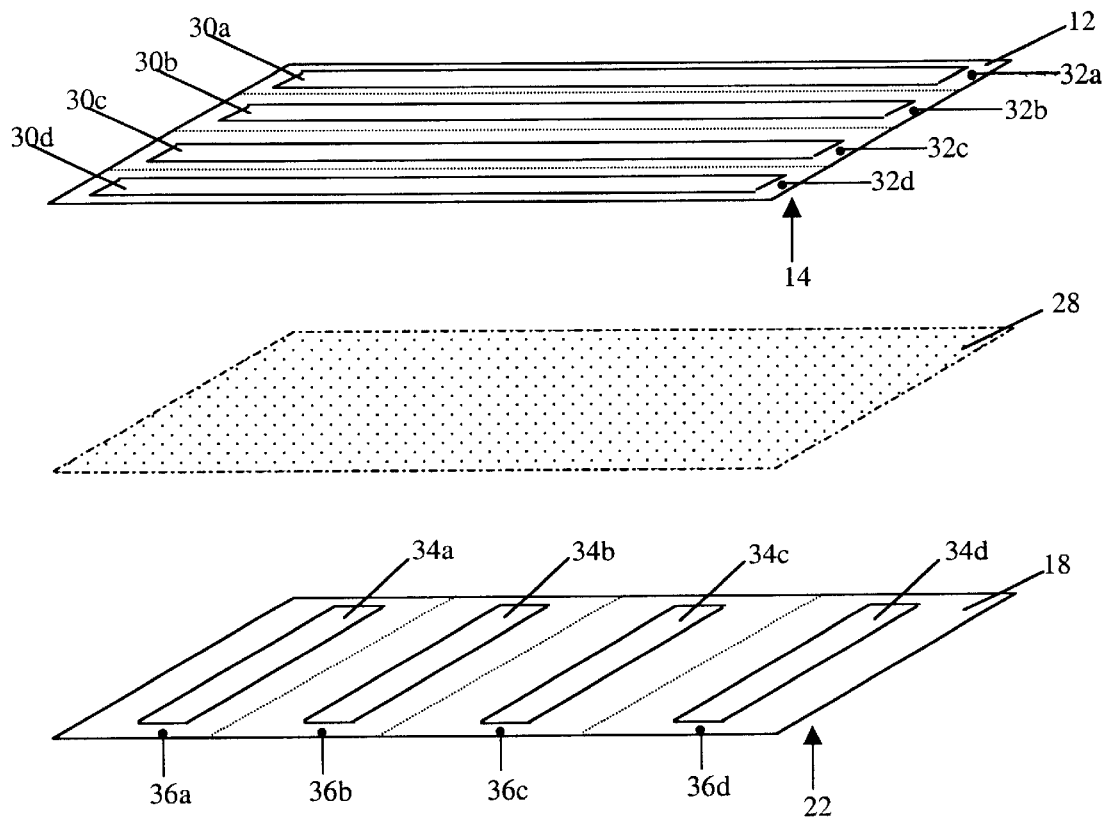
FIG. 13 is a schematic representation of a multiplex-addressing electrochromic display where an anodically coloring conjugated polymer coated on columns of a patterned ITO-coated glass electrode and a cathodically coloring conjugated polymer coated on rows of a patterned ITO-coated glass electrode, the two electrodes being spaced apart and in electrical contact with an ionic liquid therebetween as the electrolyte.

G. Fabrication of Solid-state Conjugated Polymer Electrochromic Multiplex Addressing Displays with Ionic Liquids as Electrolytes Three essential parts are required for a multiplex addressing display: an anodically coloring conjugated polymer, a cathodically coloring conjugated polymer, and an ionic liquid. Unlike the situation in a direct addressing display, conjugated polymers are coated on separate columns or rows (but not pixels) of patterned ITO-coated glass electrodes in a multiplex addressing display as illustrated in FIG. 13. Conducting polymer rows 30a–30d are generated onto ITO-coated glass electrode 12 and are independently electrically powered using electrical connections, 32a–32d, respectively, forming thereby electrode 14. Similarly, conducting polymer columns, 34a–34d are generated onto ITO-coated glass electrode 18 and are independently electrically powered through electrical connections 36a–36d, respectively, forming thereby electrode 22. Electrodes 12 and 22 are then spaced apart with ionic liquid 28 having a thickness of approximately 100 μm therebetween as the conducting electrolyte.

As an example, PANI and PEDOT were employed as anodically and cathodically coloring polymers, respectively. Both polymers were electrochemically deposited onto patterned ITO-coated glass electrodes from ionic liquids as set forth in the discussion for FIG. 4 hereof. The device fabrication procedures including polymer coating, device sealing and electrical contact formation were the same as those for the direct-addressing displays described in FIG. 8 hereof.

Figure 14:
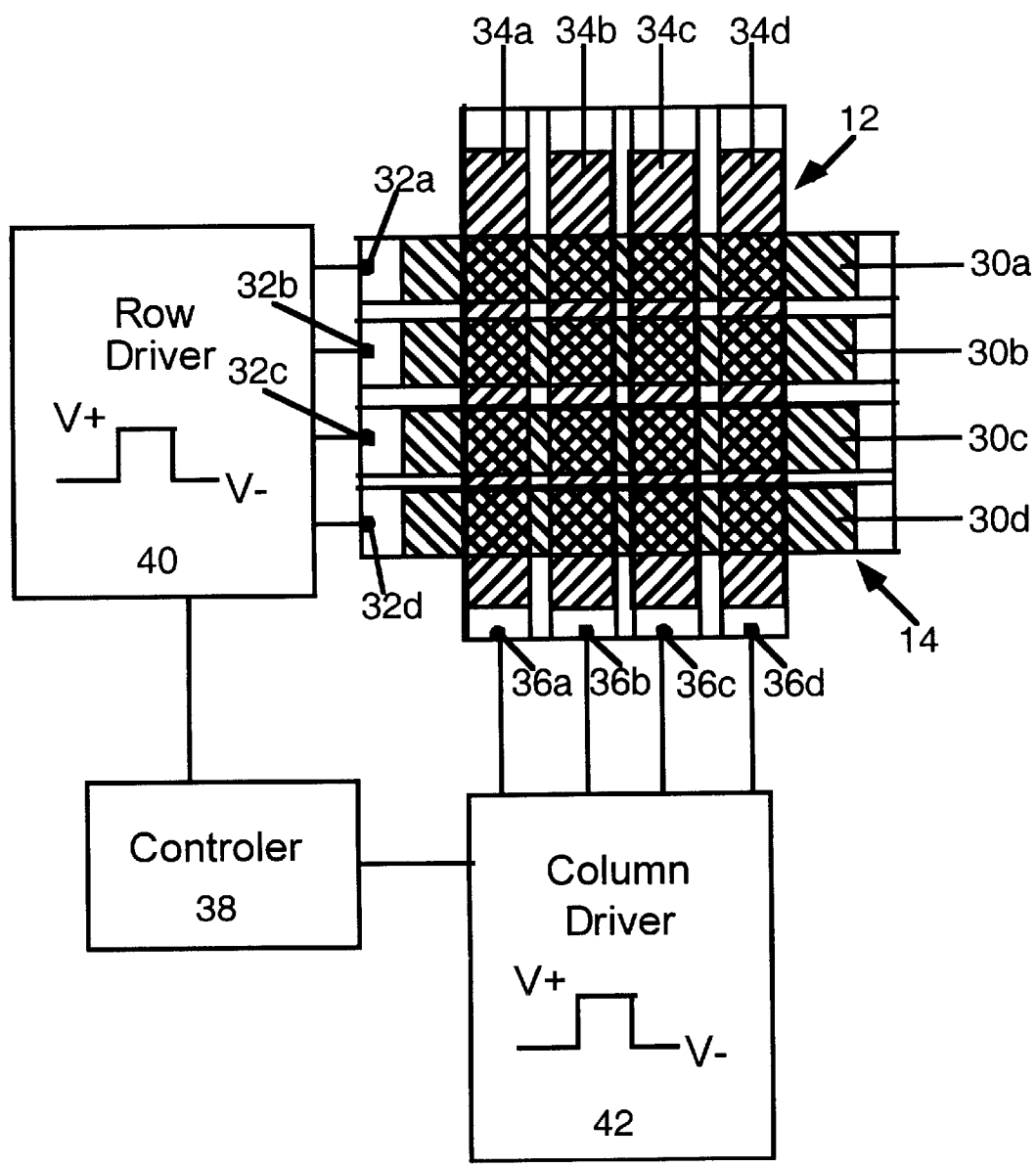
FIG. 14 shows a schematic representation of a control apparatus for operating the ionic liquid, conjugated polymer multiplex addressing electrochromic display as described in FIG. 13 hereof.

The display control apparatus shown in FIG. 14 hereof was used to select and power the desired row and column combinations to generate a desired display. Controller, 38, was used to direct voltage supplies, 40 and 42, which supply suitable voltages to rows 32a–32d and columns 34a–34d, respectively. Clearly, any number of rows and columns can be used and the number of rows and columns need not be equal.

H. Fabrication of Solid-state Conjugated Polymer Electrochromic Large Area Windows with Ionic Liquids as Electrolytes To produce large area electrochromic windows, at least two factors are important: the first is the uniform coating of conjugated polymers in large area, and the other is the high electroactivity and coloration of the resulting polymer films in the electrolytes used.

Figure 15:
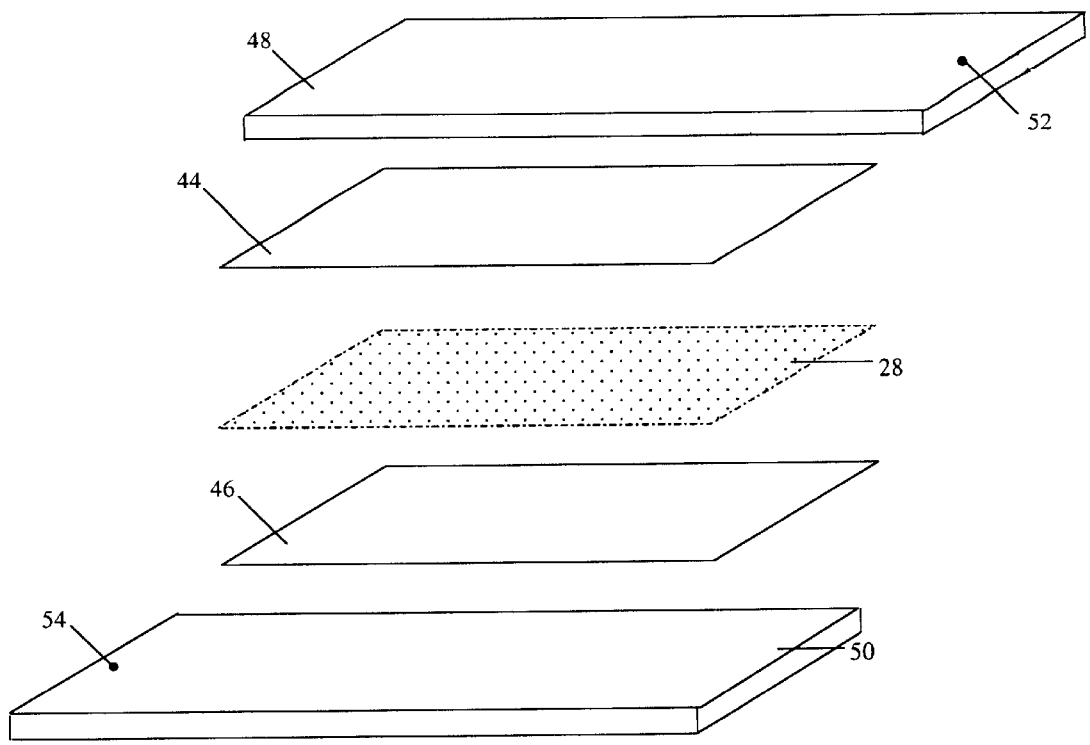
FIG. 15 is a schematic representation of an electrochromic window showing an anodically coloring conjugated polymer coated on an ITO-coated glass electrode and a cathodically coloring conjugated polymer coated on an ITO-coated glass electrode, the two electrodes being spaced apart and in electrical contact with an ionic liquid therebetween as the electrolyte.

Chemically synthesized conjugated polymers are preferable for large area electrochromic windows, although both chemically and electrochemically synthesized conjugated polymers can be used. Chemically synthesized conjugated polymers are first dissolved in an appropriate solvent and the resulting solution is used to apply the conducting polymer coating by spin-coating, dip-coating or spray-coating techniques, to name three examples of coating processes. Turning now to FIG. 15 hereof, conjugated polymers, 44 and 46, are deposited onto ITO-coated glass electrodes 48 and 50, respectively. Electrodes, 52 and 54, permit desired electrical voltages to be applied between polymers 44 and 46, respectively. The conducting polymer coated ITO-coated glass electrodes are then spaced apart with ionic liquid, 28 having a thickness of approximately 100 μm located therebetween as the electrolyte.

Figure 16:
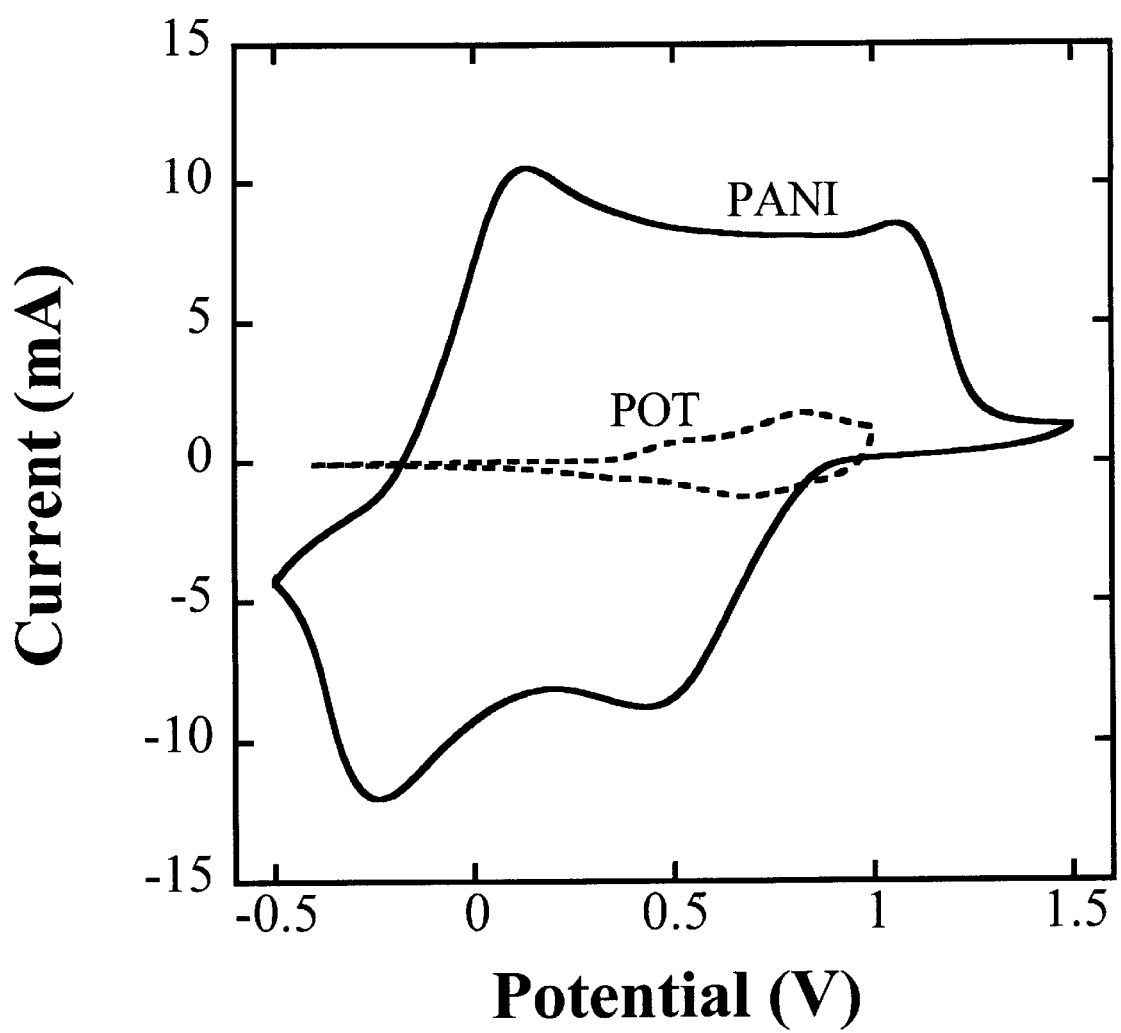
FIG. 16 shows cyclic voltammograms of spin-coated, conjugated polymer coated ITO-coated glass electrodes obtained in [BMIM][BF$_4$] with a scan rate of 50 mV/s, the surface area of each ITO-coated glass electrode being 5 cm×5 cm.

In the present invention, chemically synthesized PANI and poly(3-octylthiophene) (POT) were used as anodically and cathodically coloring polymers, respectively. They were spin-coated onto two ITO-coated glass electrodes (effective surface area 5 cm×5 cm), respectively. PANI was spin-coated at 11,000 rpm from a solution of 4% emeraldine base dissolved in a mixture of 80% formic acid and 20% dichloroacetic acid, resulting in the thickness of PANI film of 0.5 μm. POT was spin-coated at 11,000 rpm from a solution of 1% POT dissolved in $CHCl_3$, resulting in the thickness of POT film of 0.2 μm. Cyclic voltammograms for spin-coated PANI and POT coated large-area ITO-coated glass electrodes were obtained in ionic liquid [BMIM][$BF_4$] in an electrochemical cell consisting of the polymer coated ITO-coated glass electrode as working electrode, a 1.5 mm diameter platinum wire as counter electrode, and a 1.0 mm diameter silver wire as reference electrode at a scan rate of 50 mV/s, as shown in FIG. 16 hereof. Generally, cyclic voltammetric peaks become ill-defined (such as wider peak width and larger peak separation) in any electrolyte as the surface area of electrode increases. This would result in slow and non-uniform coloration of the device. However, in the ionic liquid systems employed in accordance with the teachings of the present invention, well-defined electroactivity of conjugated polymers was obtained over a large area.

Figure 17:
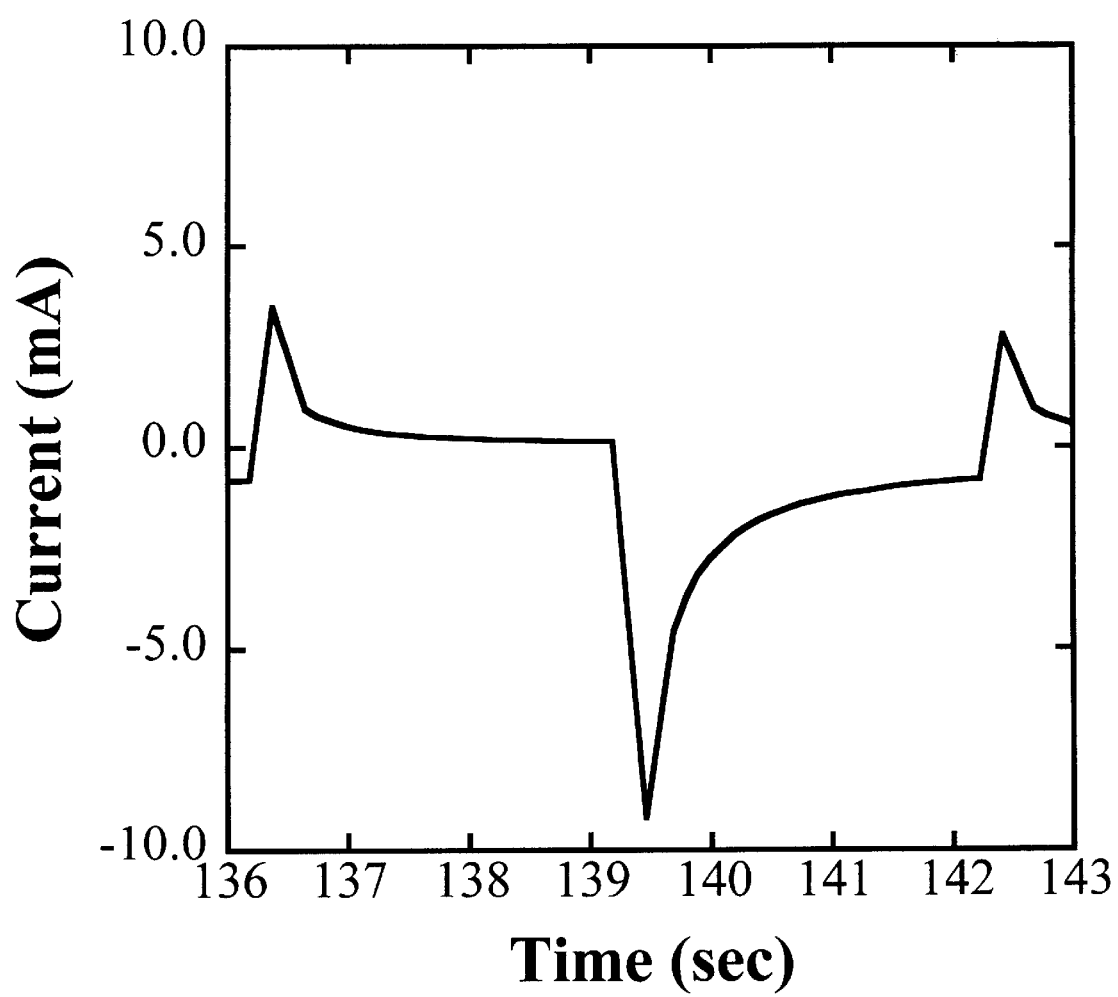
FIG. 17 shows chronoamperogram obtained upon voltage switching between −1.7 V and +1.0 V with a pulse width of 3 s for the large-area electrochromic window fabricated from two conjugated polymer coated ITO-coated glass electrodes described in FIG. 16 hereof with [BMIM][BF$_4$] as the electrolyte as described in FIG. 15.

A large area electrochromic window was fabricated from the above two conjugated polymer coated ITO-coated glass electrodes with [BMIM][$BF_4$] as the electrolyte and schematically illustrated in FIG. 15 hereof. The procedures for sealing the device and for establishing electrical contact therewith were the same as those for direct-addressing displays shown in FIG. 8 hereof. Upon voltage switching between −1.7 V and +1.0 V, with a pulse width of 3 s, fast and uniform color change from transparent yellow to blue was observe changes can be confirmed by the chronoamperogram as shown in FIG. 17 hereof. It can be seen that coloring (at +1.0V) and bleaching (at −1.7V) were completed within 1.5 s, respectively.

The foregoing description of the invention has been presented for purposes of illustration and description and is not intended to be exhaustive or to limit the invention to the precise form disclosed, and obviously many modifications and variations are possible in light of the above teaching. The embodiments were chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

What is claimed is:

1. A method for preparing an electroactive conjugated polymer which comprises the steps of:
    (a) immersing a pair of electrodes in an anhydrous ionic liquid which is stable in the presence of water containing the monomeric form of the conjugated polymer; and
    (b) applying a voltage between the electrodes in the pair of electrodes until a desired quantity of conjugated polymer which is stable in the presence of the ionic liquid is deposited on one of the electrodes in the pair of electrodes.

2. The method as described in claim 1, wherein the voltage applied between the electrodes in the pair of electrodes is selected from the group consisting of a constant voltage, a voltage which establishes a constant current between the electrodes and a voltage cycled at a chosen scan rate.

3. The method as described in claim 1, wherein the monomers of the conjugated polymers are selected from the group consisting of phenylene, phenylenevinylene, phenylenesulfide, fluorene, pyridine, pyridalvinylene, pyrrole, aniline, thiophene, thiophenevinylene, furan, acetylene, quinone, carbazole, azulene, indole and derivatives thereof.

4. The method as described in claim 1, wherein the ionic liquid comprises at least one ionic solid dissolved in an ionic liquid.

5. The method as described in claim 1, wherein the ionic liquid comprises a mixture of ionic liquids.

6. The method as described in claim 1, wherein the ionic liquid comprises compositions having at least one cation selected from the group consisting of pyridinium, pyridazinium, pyrimidinium, pyrazinium, imidazolium, pyrazolium, thiazolium, oxazolium, triazolium, ammonium, pyrrolidinium, pyrrolinium, pyrrolium, and piperidinium; and at least one anion selected from the group consisting of $F^-$; $Cl^-$; $Br^-$; $I^-$; $NO_3^-$; $N(CN)_2^-$; $BF_4^-$, $ClO_4^-$; $PF_6^-$; $RSO_3^-$; $RCOO^-$; where R is an alkyl group, substituted alkyl group, or phenyl group; $(CF_3)_2PF_4^-$, $(CF_3)_3PF_3^-$, $(CF_3)_4PF_2^-$, $(CF_3)_5PF^-$, $(CF_3)_6P^-$, $(CF_2SO_3^-)_2$, $(CF_2CF_2SO_3^-)_2$, $(CF_3SO_2)_2N^-$, $CF_3CF_2(CF_3)_2CO^-$, $(CF_3SO_2)_2CH^-$, $(SF_5)_3C^-$, $(CF_3SO_2)_3C^-$, $[O(CF_3)_2C_2(CF_3)_2O]_2PO^-$, and $CF_3(CF_2)_7SO_3^-$.

7. The method as described in claim 1, wherein the ionic liquid containing the monomeric form of polyaniline or a derivative of polyaniline further comprises an acid suitable for enabling monomer protonation.

8. The method as described in claim 7, wherein the ionic liquid containing the monomeric form of the conjugated polymer comprises [BMIM][BF$_4$] for pyrrole and 3,4-ethylenedioxythiophene, where BMIM is 1-butyl-3-methylimidazolium; and CF$_3$COOH dissolved in [BMIM][BF$_4$] for aniline.

9. The method as described in claim 1, wherein the electrodes in the pair of electrodes are selected from the group consisting of platinum, gold, carbon and ITO.

10. An electrochromic device, comprising in combination:
    (a) a first electrically conducting substrate;
    (b) a second electrically conducting substrate spaced apart from said first substrate;
    (c) a first conjugated polymer deposited onto the surface of said first substrate facing said second substrate;
    (d) a second conjugated polymer deposited onto the surface of said second substrate facing said first substrate;
    (e) an ionic liquid electrolyte not containing a polymer additive, disposed between and in electrical contact with said first conjugated polymer and said second conjugated polymer; and
    (f) an electrical power supply for applying a voltage between said first substrate and said second substrate.

11. The device as described in claim 10, wherein said first conjugated polymer and said second conjugated polymer are stable in the presence of the ionic liquid, and said ionic liquid is stable in the presence of water.

12. The device as described in claim 10, wherein said first conjugated polymer comprises an anodically coloring conjugated polymer and said second conjugated polymer comprises a cathodically coloring conjugated polymer.

13. The device as described in claim 12, wherein said first conjugated polymer comprises polyaniline and said second conjugated polymer comprises poly(3,4-ethylenedioxythiophene).

14. The device as described in claim 12, wherein said first conjugated polymer comprises polyaniline and said second conjugated polymer comprises poly(3-octylthiophene).

15. The device as described in claim 10, wherein said ionic liquid comprises compositions having at least one cation selected from the group consisting of pyridinium, pyridazinium, pyrimidinium, pyrazinium, imidazolium, pyrazolium, thiazolium, oxazolium, triazolium, ammonium, pyrrolidinium, pyrrolinium, pyrrolium, and piperidinium; and at least one anion selected from the group consisting of $F^-$; $Cl^-$; $Br^-$; $I^-$; $NO_3^-$; $N(CN)_2^-$; $BF_4^-$, $ClO_4^-$, $PF_6^-$, $RSO_3^-$, $RCOO^-$, where R is an alkyl group, substituted alkyl group, or phenyl group; $(CF_3)_2PF_4^-$, $(CF_3)_3PF_3^-$, $(CF_3)_4PF_2^-$, $(CF_3)_5PF^-$, $(CF_3)_6P^-$, $(CF_2SO_3^-)_2$, $(CF_2CF_2SO_3^-)_2$, $(CF_3SO_2)_2N^-$, $CF_3CF_2(CF_3)_2CO^-$, $(CF_3SO_2)_2CH^-$, $(SF_5)_3C^-$, $(CF_3SO_2)_3C^-$, $[O(CF_3)_2C_2(CF_3)_2O]_2PO^-$, and $CF_3(CF_2)_7SO_3^-$.

16. The device as described in claim 15, wherein the ionic liquid comprises 1-butyl-3-methylimidazolium.

17. The device as described in claim 10, wherein said first substrate and said second substrate comprise conducting and optically transparent substrates.

18. The device as described in claim 17, wherein said first substrate and said second substrate comprise ITO-coated glass.

19. The device as described in claim 10, wherein said first conjugated polymer is electrochemically deposited onto said first substrate and said second conjugated polymer is electrochemically deposited onto said second substrate.

20. The device as described in claim 10, wherein said first conjugated polymer is mechanically deposited onto said first substrate and said second conjugated polymer is mechanically deposited onto said second substrate.

* * * * *